US007736878B2

(12) United States Patent
Yarosh et al.

(10) Patent No.: US 7,736,878 B2
(45) Date of Patent: Jun. 15, 2010

(54) PRODUCTION OF CPD GLYCOSYLASES

(75) Inventors: Daniel B. Yarosh, Merrick, NY (US); Leonard F. Estis, Coram, NY (US); Eliyahu Kraus, Sutton, MA (US)

(73) Assignee: Applied Genetics Incorporated Dermatics, Freeport, NY (US)

( * ) Notice: Subject to any disclaimer, the term of this patent is extended or adjusted under 35 U.S.C. 154(b) by 381 days.

(21) Appl. No.: 11/478,293

(22) Filed: Jun. 29, 2006

(65) Prior Publication Data

US 2007/0077621 A1 Apr. 5, 2007

Related U.S. Application Data

(60) Provisional application No. 60/696,256, filed on Jul. 1, 2005.

(51) Int. Cl.
C12N 9/24 (2006.01)
C12N 9/00 (2006.01)
C12N 1/20 (2006.01)
C12N 15/00 (2006.01)
C12P 21/06 (2006.01)
C07H 21/04 (2006.01)

(52) U.S. Cl. ............... 435/200; 435/69.1; 435/183; 435/252.3; 435/320.1; 536/23.2

(58) Field of Classification Search ................ None
See application file for complete search history.

(56) References Cited

U.S. PATENT DOCUMENTS

| 5,077,211 A | 12/1991 | Yarosh |
| 5,296,231 A | 3/1994 | Yarosh |
| 5,302,389 A | 4/1994 | Kripke et al. |
| 5,308,762 A | 5/1994 | Lloyd |

FOREIGN PATENT DOCUMENTS

WO WO 01/90332 11/2001

OTHER PUBLICATIONS

Inaoka et al., Affinity of single-or double-stranded oligodeoxyribonucleotides containing a thymine phtodimer for T4 Endonuclease V. J. Biol. Chem., 1989, vol. 264 (5): 2609-2614.*
Gustaffson et al., Codon bias and heterologous protein expression. Trends in Biotechnol., Jul. 2004, vol. 22 (7): 346-353.*
Sharp et al., Variation in the strength of selected codon usage bias among bacteria. Nuc. Acids Res., 2005, vol. 33 (4): 1141-1153, published online Feb. 23, 2005.*
Broun et al., Catalytic plasticity of fatty acid modification enzymes underlying chemical diversity of plant lipids. Science, 1998, vol. 282: 1315-1317.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol.,2001, vol. 183 (8): 2405-2410.*
Witkowski et al., Conversion of b-ketoacyl synthase to a Malonyl Decarboxylase by replacement of the active cysteine with glutamine. Biochemistry, 1999, vol. 38: 11643-11650.*
Latham, et al.; T4 Endonuclease V; Perspectives on Catalysis; DNA Damage-Effects on DNA Structure and Protein Recognition; Annals of New York Academy of Science; vol. 726, pp. 181-197; 1994.
Augustine, et al.; Oligonucleotide Site Directed Mutagenesis of All Histidine Residues within the T4 Endonuclease V Gene: Role in Enzyme-Nontarget DNA Binding; Biochemistry; vol. 30; pp. 8052-8059; 1991.
Chenevert, et al.; Partial complementation of the UV sensitivity of *E. coli* and yeast excision repair mutants by the cloned denV gene of bacteriophage T4; Molecular and General Genetics; 203:163-171; 1986.
Dodson, et al.; Structure-function studies of the T4 endonuclease V repair enzyme; Mutation Research; 218; pp. 49-65; 1989.
Doi, et al.; Role of the basic amino acid cluster and Glu-23 in pyrimidine dimer glycosylase activity of T4 endonuclease V; Proceedings of the National Academy of Sciences USA; vol. 89 pp. 9420-9424; 1992.
Green, et al.; Structure/function analysis of the $Ala^{116} \rightarrow Lys^{121}$ region of endonuclease V by random targeted mutagenenesis; Nucleic Acids Research; vol. 21; No. 3; pp. 727-732; 1993.
Gustafsson, Claes, Ph.D.; Protein Expression Using Synthetic Genes; Genetic Engineering News; Drug Discovery; vol. 25; No. 5; p. 32; 2005.
Hesterberg, et al.; High-Hydrostatic Pressure Refolding of Proteins; Genetic Engineering News; Bioprocessing; vol. 25; No. 4; pp. 46-47; 2005.
Hori, et al.; Participation of glutamic acid 23 of T4 endonuclease V in the β-elimination reaction of an abasic site in a synthetic duplex DNA; Nucleic Acids Research; vol. 20; No. 18; pp. 4761-4764; 1992.
Ishida, et al.; In Vitro and In Vivo Activities of T4 Endonuclease V Mutants Altered in the C-Terminal Aromatic Region; Biochemistry; 29; pp. 3817-3821; 1990.
Lapointe, et al.; Tobacco plants expressing T4 endonuclease V show enhanced sensitivity to ultraviolet light and DNA alkylating agents; Mutation Research; Fundamental and Molecular Mechanisms of Mutagenesis; 351; pp. 19-31; 1996.
Liebig, et al.; Bacteriophage T4 Early Promoter Regions; Consensus Sequences of Promoters and Ribosome-binding Sites; Journal of Molecular Biology; 208; pp. 517-536; 1989.
Liszewski, Kathy; Emerging Protein-Expression Technologies; Innovations in Vectors, Production Systems, and Purification; Genetic Engineering News; vol. 23; No. 18; p. 34; 2003.

(Continued)

*Primary Examiner*—Ganapathirama Raghu
(74) *Attorney, Agent, or Firm*—Yongzhi Yang

(57) ABSTRACT

Recombinant forms of DNA sequences for CPD glycosylases, including the bacteriophage T4 gene denV, are described that are capable of expression at high levels. Active CPD glycosylases can be recovered from inclusion bodies resulting from the high expression using, for example, a homogenization process which employs stream mixing, and the active proteins can be used in, for example, topical formulations for treatment of photosensitive diseases. Stream mixing can also be used to solubilize inclusion bodies containing proteins other than CPD glycosylases.

16 Claims, 3 Drawing Sheets

OTHER PUBLICATIONS

Figure 2:
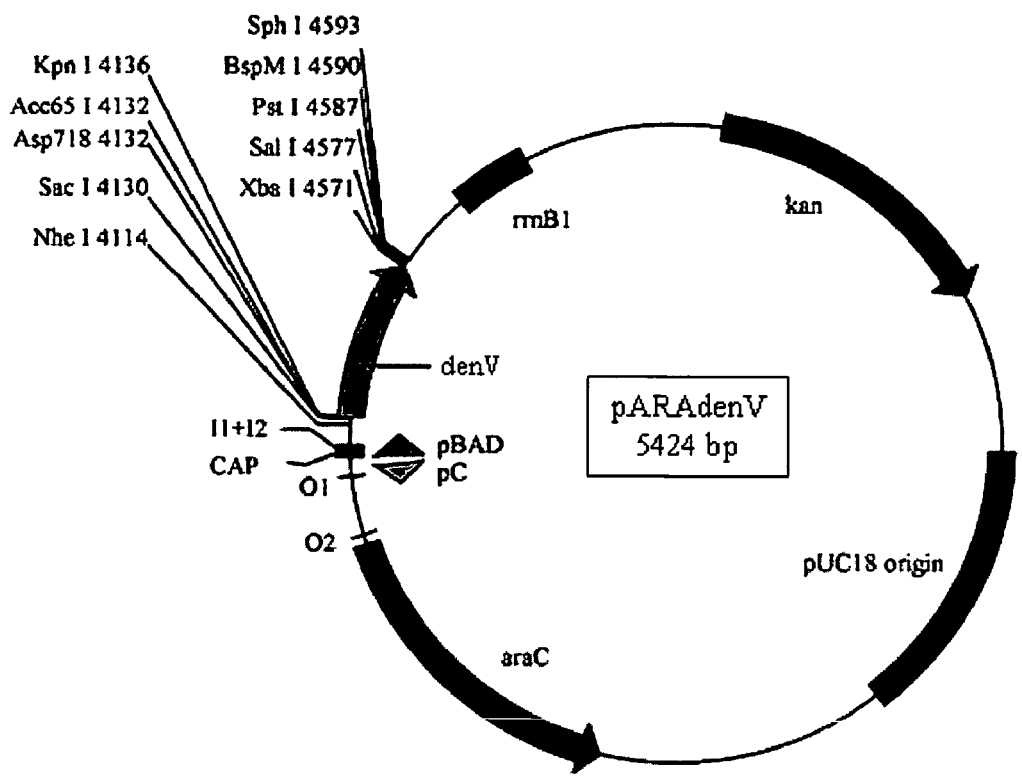

Lloyd, et al.; Expression of the denV gene of bacteriophage T4 cloned in *Escherichia coli*; Proceedings of the National Academy of Sciences USA; vol. 78; No. 5; pp. 2796-2800; 1981.

Radany, et al.; Physical Mapping and Complete Nucleotide Sequence of the denV Gene of Bacteriophage T4; Journal of Virology; vol. 52; No. 3; pp. 846-856; 1984.

Recinos, et al.; Expression of the Bacteriophage T4 denV Structural Gene in *Escherichia coli*; Journal of Bacteriology; vol. 168; No. 2; pp. 1014-1018; 1986.

Ronen, et al.; Human DNA Repair Genes; Environmental and Molecular Mutagenesis; 37:241-283; 2001.

Sancar, et al.; Molecular Mechanisms of Mammalian DNA Repair and the DNA Damage Checkpoints; Annual Review of Biochemistry; 73:39-85; 2004.

St. John, et al.; High pressue fosters protein refolding from aggregates at high concentrations; Proceedings National Academy Science USA; Vol. 96; No. 23; pp. 13029-13033; 1999.

Valerie, et al.; Identification, physical map location and sequence of the denV gene from bacteriophage T4; Nucleic Acids Research; vol. 12; No. 21; pp. 8085-8096; 1984.

Valerie, et al.; Nucleotide sequence and analysis of the 58.3 to 65.5-kb early region of bacteriophage T4; Nucleic Acids Research; vol. 14; No. 21; pp. 8637-8654; 1986a.

Valerie, et al.; Expression of the denV Gene of Coliphage T4 in UV-Sensitive rad Mutants of *Saccharomyces cerevisiae*; Molecular and Cellular Biology; vol. 6; No. 10; pp. 3559-3562; 1986b.

Yarosh, et al.; Measurement of UVB-induced DNA damage and its consequences in models of immunosuppression; Methods; 28; pp. 55-62; 2002.

Yarosh, et al.; Potoprotection by Topical DNA Repair Enzymes: Molecular Correlates of Clinical Studies; Photochemistry and Photobiology; 69(2); pp. 136-140; 1999.

Repoila, et al.; Genomic polymorphism in the T-even bacteriophages; the EMBO Journal; vol. 13; No. 17; pp. 4181-4192; 1994.

Manuel, et al.; Involvement of Glutamic Acid 23 in the Catalystic Mechanism of T4 Endonuclease V; Journal of Biological Chemistry; Vol. 270; No. 6; pp. 2652-2661; 1995.

PCT International Search Report; International Application No. PCT/US06/25561; Completion Date: Jun. 21, 2007; Date of Mailing: Aug. 3, 2007.

PCT Written Opinion Of the International Searching Authority, Or The Declaration; International Application No. PCT/US06/25561; Completion Date: Jun. 21, 2007; Mailing Date: Aug. 3, 2007.

Supplementary European Search Report; EP Application No. EP 06785950; Completion Date: Apr. 7, 2009; Date of Mailing: Apr. 22, 2009.

Lloyd, R. Stephen; Review; Investigations of pyrimidine dimer glycosylases—a paradigm for DNA base excision repair enzymology; Mutation Research; vol. 577; pp. 77-91; Available on-line at www.sciencedirect.com; 2005.

* cited by examiner

|    |        | MET | THR | ARG | ILE | ASN | LEU | THR | LEU | VAL | SER |    |
|----|--------|-----|-----|-----|-----|-----|-----|-----|-----|-----|-----|----|
| 1  |        | ATG | ACT | CGT | ATC | AAC | CTT | ACT | TTA | GTA | TCT | 10 |
|    | Inaoka |     | G   |     |     |     |     |     |     |     |     |    |
|    | AGI    |     | C   |     |     |     | G   | C   | C G | T   | C   |    |

|    |        | GLU | LEU | ALA | ASP | GLN | HIS | LEU | MET | ALA | GLU |    |
|----|--------|-----|-----|-----|-----|-----|-----|-----|-----|-----|-----|----|
| 11 |        | GAA | TTG | GCT | GAC | CAA | CAC | TTA | ATG | GCT | GAA | 20 |
|    | Inaoka | G   | A   |     |     |     |     |     |     |     |     |    |
|    | AGI    |     | C   |     |     |     | G   | C G |     |     |     |    |

|    |        | TYR | ARG | GLU | LEU | PRO | ARG | VAL | PHE | GLY | ALA |    |
|----|--------|-----|-----|-----|-----|-----|-----|-----|-----|-----|-----|----|
| 21 |        | TAT | CGT | GAA | TTG | CCG | CGT | GTT | TTT | GGT | GCA | 30 |
|    | Inaoka | C   |     |     |     |     |     |     |     |     |     |    |
|    | AGI    | C   |     |     | C   |     |     |     | C   |     | T   |    |

|    |        | VAL | ARG | LYS | HIS | VAL | ALA | ASN | GLY | LYS | ARG |    |
|----|--------|-----|-----|-----|-----|-----|-----|-----|-----|-----|-----|----|
| 31 |        | GTT | CGT | AAG | CAT | GTT | GCT | AAC | GGT | AAA | CGT | 40 |
|    | Inaoka |     |     |     | C   | A   | A   |     |     |     |     |    |
|    | AGI    | A   |     | A   | C   |     |     |     |     |     |     |    |

|    |        | VAL | ARG | ASP | PHE | LYS | ILE | SER | PRO | THR | PHE |    |
|----|--------|-----|-----|-----|-----|-----|-----|-----|-----|-----|-----|----|
| 41 |        | GTT | CGT | GAT | TTC | AAA | ATC | AGT | CCT | ACT | TTT | 50 |
|    | Inaoka |     |     |     |     |     |     |     |     |     |     |    |
|    | AGI    |     |     | C   |     |     |     | TC  | G   | C   | C   |    |

|    |        | ILE | LEU | GLY | ALA | GLY | HIS | VAL | THR | PHE | PHE |    |
|----|--------|-----|-----|-----|-----|-----|-----|-----|-----|-----|-----|----|
| 51 |        | ATC | CTT | GGC | GCA | GGT | CAT | GTT | ACA | TTC | TTT | 60 |
|    | Inaoka |     |     |     |     |     |     |     |     |     | C   |    |
|    | AGI    |     | G   | T'  | T   |     | C   |     | C   |     |     |    |

|    |        | TYR | ASP | LYS | LEU | GLU | PHE | LEU | ARG | LYS | ARG |    |
|----|--------|-----|-----|-----|-----|-----|-----|-----|-----|-----|-----|----|
| 61 |        | TAC | GAT | AAG | CTC | GAG | TTC | TTA | CGT | AAA | CGT | 70 |
|    | Inaoka |     |     |     |     |     |     |     | C   | G   |     |    |
|    | AGI    |     | C   | A   | G   | A   |     | C G |     |     |     |    |

|    |        | GLN | ILE | GLU | LEU | ILE | ALA | GLU | CYS | LEU | LYS |    |
|----|--------|-----|-----|-----|-----|-----|-----|-----|-----|-----|-----|----|
| 71 |        | CAA | ATC | GAG | CTT | ATA | GCT | GAA | TGT | TTA | AAA | 80 |
|    | Inaoka |     |     |     |     |     |     |     |     | G   |     |    |
|    | AGI    | G   | T   | A   | G   | C   |     |     | C   | C G |     |    |

FIG. 1A

| | | ARG | GLY | PHE | ASN | ILE | LYS | ASP | THR | THR | VAL | |
|---|---|---|---|---|---|---|---|---|---|---|---|---|
| 81 | | CGT | GGT | TTT | AAT | ATC | AAG | GAT | ACT | ACA | GTC | 90 |
| Inaoka | | | | C | | | | | | | | |
| AGI | | | | C | C | | A | C | C | T | T | |

| | | GLN | ASP | ILE | SER | ASP | ILE | PRO | GLN | GLU | PHE | |
|---|---|---|---|---|---|---|---|---|---|---|---|---|
| 91 | | CAG | GAT | ATT | AGT | GAT | ATT | CCT | CAG | GAA | TTC | 100 |
| Inaoka | | | C | C | | C | | | A | | | |
| AGI | | | | C | TC | C | C | G | | | | |

| | | ARG | GLY | ASP | TYR | ILE | PRO | HIS | GLU | ALA | SER | |
|---|---|---|---|---|---|---|---|---|---|---|---|---|
| 101 | | CGT | GGT | GAT | TAT | ATT | CCC | CAT | GAA | GCT | TCT | 110 |
| Inaoka | | | | | | | | | | | | |
| AGI | | | | C | C | C | G | C | | | | |

| | | ILE | ALA | ILE | SER | GLN | ALA | ARG | LEU | ASP | GLU | |
|---|---|---|---|---|---|---|---|---|---|---|---|---|
| 111 | | ATT | GCT | ATA | TCA | CAA | GCT | CGT | TTA | GAT | GAA | 120 |
| Inaoka | | | | | | | | | | | | |
| AGI | | C | A | C | T | G | | | C G | C | | |

| | | | | | | | | | | PHE | | |
|---|---|---|---|---|---|---|---|---|---|---|---|---|
| US '762 | | LYS | ILE | ALA | GLN | ARG | PRO | THR | TRP | TYR | LYS | |
| 121 | | AAA | ATT | GCA | CAA | CGT | CCT | ACT | TGG | TAC | AAA | 130 |
| Inaoka | | | | | | | | | | | | |
| AGI | | | C | T | G | | G | C | | | | |

| | | TYR | TYR | GLY | LYS | ALA | ILE | TYR | ALA | term | | |
|---|---|---|---|---|---|---|---|---|---|---|---|---|
| 131 | | TAC | TAC | GGT | AAG | GCG | ATT | TAT | GCA | TAA | | 138 |
| Inaoka | | | | | | | | | | G | | |
| AGI | | T | | | A | A | C | C | T | | | |

The native *denV* gene sequence is shown in bold letters. The numbers of the amino acids at the beginning and end of each line are shown. The sequence changes are for the Inaoka et al. synthetic gene (Inaoka), and for the new synthetic gene in accordance with the present invention (AGI). The US '762 patent claims a change in the amino acid at 129 from TYR to PHE. The final codon TAA is a termination codon (term).

FIG. 1B

| Mapped Functional Regions in pARAdenV | | | |
|---|---|---|---|
| Name | Start | End | Size |
| kanamycin resistance | 123 | 938 | 816 |
| pUC18 origin | 1379 | 2136 | 758 |
| araC | 3787 | 2909 | 879 |
| O2 operator | 3833 | 3816 | 18 |
| pC promoter | 3966 | 3938 | 29 |
| O1 operator | 3995 | 3974 | 22 |
| CAP site | 4017 | 4030 | 14 |
| I1 + I2 operator | 4026 | 4064 | 39 |
| pBAD promoter | 4063 | 4090 | 26 |
| denV gene | 4137 | 4569 | 433 |
| rrnB1 terminator | 4805 | 5007 | 203 |

PRODUCTION OF CPD GLYCOSYLASES

CROSS REFERENCE TO RELATED APPLICATION

This application claims the benefit under 35 USC §119(e) of U.S. Provisional Application No. 60/696,256 filed Jul. 1, 2005, the contents of which in its entirety is hereby incorporated by reference.

I. FIELD OF THE INVENTION

This invention relates to the production of CPD glycosylases. More particular, in accordance with certain of its aspects, the invention relates to expression of genes coding for CPD glycosylases. In accordance with further aspects, it relates to methods for achieving recovery of enzyme activity of expressed CPD glycosylases and other proteins.

II. DEFINITIONS

As used herein, the following terms and phrases shall have the following meanings:

The word "protein" is used broadly and includes any molecule that includes a sequence of two or more amino acids connected together. A "protein" thus includes, without limitation, a peptide, a polypeptide, a protein as conventionally known, and a complex of peptides, polypeptides, and/or proteins.

A "CPD glycosylase protein" is a protein that binds to a cyclobutane pyrimidine dimer in DNA and produces an alkaline-labile site in the DNA at the site of the cyclobutane pyrimidine dimer.

An "alkaline-labile site" is a site which can be cleaved by alkaline conditions, or by the CPD glycosylase, or by another protein with apurinic/apyrimidinic endonuclease activity to produce a DNA strand break.

As discussed in the literature (for example, see Dodson and Lloyd, 1989), it is currently believed that the glycosylase action of a CPD glycosylase is mediated via an imino intermediate between the C1' of the sugar of the DNA and an amino group in the glycosylase. For typical CPD glycosylases, β-elimination reaction then follows at the resulting abasic site, causing a cleavage of the phosphodiester bond of the DNA.

A "stream mixer" is a mixing device wherein at least part of the mixing comprises: (1) forming two or more flowing streams, which may have the same or different compositions, and (2) impinging the streams on one another.

III. BACKGROUND OF THE INVENTION

A. The CPD Glycosylase DNA Repair Enzymes

DNA repair is a function essential to every living organism. A DNA repair enzyme is a protein which contributes to the restoration of damaged DNA to its native state. See Ronen and Glickman, 2001; Sancar et al., 2004; J. A. Nickoloff and M. F. Hoekstra, eds., *DNA Damage and Repair, Volumes I and II*, 1998. The types of DNA repair enzymes found in human and mammalian cells generally are found in other organisms. Additional types of DNA repair enzymes may be found in non-mammalian organisms, such as photolyases.

Particularly important DNA repair enzymes are the cyclobutane pyrimidine dimer glycosylases, known as CPD glycosylases. For example, the CPD glycosylase product of the bacteriophage T4 denV gene, specifically known as T4 endonuclease V, has become an important protein with wide application in research and in emerging pharmaceutical products (see U.S. Pat. Nos. '211, '231, '389).

The CPD glycosylases have a specificity for cyclobutane pyrimidine dimers in DNA in which, as currently understood in the art, the glycosylase action is mediated via an imino intermediate between the C1' of the sugar of the DNA and an amino group in the glycosylase, followed typically by a β-elimination reaction resulting in cleavage of the phosphodiester bond of the DNA. As also currently understood in the art, the protein releases the 5' pyrimidine of the cyclobutane pyrimidine dimer from the sugar of the DNA (hence the term glycosylase), which creates an apyrimidinic site in the DNA which is very sensitive to hydrolysis under alkaline conditions. CPD glycosylases have been identified in many different organisms, in some cases by purification, in other cases by detecting the unique activity of this protein in an extract, and in still other cases, the presence of the protein has been deduced from the close homology of the putative amino acid sequence of the protein coded by a nucleotide sequence to known CPD glycosylase proteins.

Attempts to express the CPD glycosylase, T4 endonuclease V, in large amounts have been disappointing. After bacteriophage T4 DNA enters its *E. coli* host, the denV gene is transcribed to produce T4 endonuclease V only within the first 2 minutes of infection. The first DNA clones containing the denV gene were unstable (Lloyd and Hanawalt, 1981). Stable cloning of the entire intact gene has proved to be impossible because the nucleotide sequences in this region of the phage genome are lethal to the host, and scientists have speculated that it is likely because the endogenous promoter is too strong for constitutive expression in *E. coli* (Valerie et al., 1986a, Chenevert, 1986). In fact, sequence analysis of the early gene promoters, including the denV promoter, shows that their consensus sequence is significantly different than that of the host consensus promoter sequence derived from analysis of 112 *E. coli* genes (Liebig and Rüiger, 1989). These authors note that "strong promoters can be cloned stably only when one or several strong terminators of transcription are inserted downstream from the cloning site" (p532).

Ultimately the native denV structural gene was cloned by piecing together fragments of the gene without its native promoter (Valerie et al.; 1984; Radany et al., 1984). The sequence is listed in the National Center for Biotechnology Information Gene database as GeneID 1258606, and it is the native structural gene sequence without the promoter that we refer to herein as the native denV gene.

Once cloned, the native denV gene was placed downstream of various promoters. In one case, the gene was positioned downstream of the λ phage leftward operator and the rightward promoter ($O_L P_R$; Recinos et al., 1986). Expression from the unrepressed promoter in a variety of *E. coli* host strains resulted in T4 endonuclease V levels no more than 0.2% of total cellular protein. Growth temperatures above 25° C. and glucose levels above 0.05% inhibited denV gene expression, although these conditions are ordinarily beneficial to the host cell growth.

In a second case, the native denV gene was placed under the control of the *E. coli* TAC promoter, whose expression is induced by the lactose analog isopropyl-thiogalactoside (IPTG; Chenevert et al., 1986). Induction of T4 endonuclease V from this expression vector in *E. coli* produced filamentation and cell death. Chenevert et al. report that the denV protein was 10% of the total cell protein based on a single gel (Chenevert et al., 1986: FIG. 5). In connection with the development of the present invention, more than a dozen fermentations at commercial scale showed that this expression vector is only able to produce T4 endonuclease V at about 1% of total protein (see Table 8 of Example 4 below).

Chenevert et al. also cloned the native denV gene under the control of the yeast GAL1 and ADH promoters; however, they reported neither the efficiency of expression of T4 endonuclease V nor the effect on cell growth in induced yeast (Chenevert et al., 1986). Significantly, they reported that the construct made wild type yeast more sensitive to UV, not more resistant as would be expected if the expressed enzyme was compatible with cell viability. Valerie et al. (1986b) cloned the native denV gene under the control of the yeast AAH5 promoter, and they found that the induced construct did not change the growth characteristics or cell morphology of the yeast host. They reported that the T4 endonuclease was estimated to be "several percent" of total protein by scanning of a single gel (Valerie et al. 1986b: FIG. 2), but this may be an overestimate since the gel is clearly overloaded with protein. They found that the construct in UV-sensitive yeast recombinants increased UV resistance.

The native denV gene has also been placed under the control of a CaMV 35S promoter and transferred into tobacco plants (Lapointe et al., 1996). The amount of T4 endonuclease V produced in the plant was not reported. As in the case of some yeast systems, the construct increased, rather than decreased, the sensitivity of the plants to UV and alkylating agents, i.e., the construct lacked DNA repair activity.

Attempts to improve T4 endonuclease V by changing the native denV gene nucleic acid sequence, resulting in a change in the amino acid sequence, have not met with success. For over a decade, the Lloyd laboratory modified the T4 endonuclease V amino acid sequence either by recombinant selection or by site-directed mutagenesis. Dodson and Lloyd (1989) summarized the effect of changes in the amino acid sequence on T4 endonuclease V activity. None of the dozens of recombinants that were reviewed showed greater activity than the native denV sequence, and many proved to be unstable in the cell.

Other laboratories, such as the Henderson laboratory (Green et al., 1993) and the Ohtsuka laboratory (Ishida et al., 1990; Doi et al., 1992; Hori et al., 1992) made numerous changes in the sequence of the native denV gene, resulting in substitutions in the amino acid sequence of the enzyme, all without significantly increasing the enzyme activity. The single exception from the Lloyd laboratory was a change in tyrosine at position 129 to a less polar aromatic amino acid, such as phenylalanine (see U.S. Pat. No. 5,308,762). This resulted in an increase in specific activity, but only under conditions of low salt. As these are not physiological conditions, this recombinant enzyme has no therapeutic value.

Attempts have been made to change the nucleotide sequence of the native denV without altering the amino acid sequence, but they have been unsuccessful. The first attempt was to change two AUA isoleucine codons (nucleotides 103-105, 137-139) to the AUC triplet, which did not change expression levels (Recinos et al., 1986). The Ohtsuka laboratory constructed a synthetic denV gene. They did not change the amino acid sequence, but did change the nucleotide sequence, for the purpose in their words, "to introduce extra restriction sites and to facilitate enzymatic rejoining with DNA ligase by avoiding self-complementary joining sites" (Inaoka et al., 1989). The gene was cloned under control of the trp promoter, and after induction the amount of T4 endonuclease V was reported to be about 15% of the total protein.

Standard expression systems for T4 endonuclease V or even Inaoka et al.'s system (collectively, systems which produce T4 endonuclease V at a level less than or equal to 15 percent of total protein) are unsatisfactory for commercial purposes, e.g., pharmaceutical purposes. Host *E. coli* contain the HU-α protein that is very similar in size and charge to T4 endonuclease V, and this protein contaminates preparations of T4 endonuclease V. These contaminants are not sufficiently removed by standard purification methods used in industrial scale purification, such as size exclusion or ion exchange. The resulting preparations inevitably contain >10% HU-α contamination.

The commercial practitioner is thus faced with a dilemma: it can increase purity by reducing the yield, but this makes the product too costly for commercialization; or it can increase the yield by reducing the purity, but this makes the product unacceptably contaminated for pharmaceutical use.

B. High Expression and the Production of Inclusion Bodies

In addition to the foregoing difficulties, high expression of proteins in-host cells causes the proteins to be expressed as inclusion bodies. These are precipitated or coagulated accumulations of inactive proteins that are insoluble. Inclusion bodies therefore are lost to further purification, and the increased production of a protein from an expression vector is of no value if the proteins are not recovered and/or they are not in active form. Inclusion bodies are a significant problem for high expression vector systems.

Prior attempts to deal with the inclusion problem have included the use of high hydrostatic pressure to refold protein aggregates (St. John et al., 1999; Hesterberg et al., 2005). This process is unsatisfactory for three main reasons: (1) the process uses volumes that are fixed by the size of the vessel, which is especially problematic in scaling up to commercial volumes, because each increase in scale requires that a new vessel must be built and validated; (2) the high pressure of the hydrostatic pressure method (29,000 psi) is more difficult and costly to achieve and maintain than lower pressures; and (3) the hydrostatic method still requires that the cells be lysed before processing.

As recently discussed by Kathy Liszewski in the Oct. 15, 2003 edition of *Genetic Engineering News*, there is no universal solution to the inclusion body problem. The approach by the current state of the art is to recover the inclusion bodies and attempt to refold them. Lieszweski quotes Paul Haney, Ph.D., senior research scientist at Pierce Biotechnology as saying, "Refolding proteins can be a cumbersome and time-consuming task, since refolding conditions have to be optimized for each protein in order to promote formation of the native fold and to prevent protein aggregation. There is no universal refolding buffer system." The solution thus must be found for each individual protein, and there is no guarantee that a solution can be found.

C. Summary of the State of the Art

As shown by the history of the cloning of T4 endonuclease V set forth above and as discussed by Dr. Claes Gustafsson in *Genetic Engineering News*, 2005, the design of expression vectors is not at all an exact or routine undertaking. Consequently, high expression vectors for CPD glycosylases and, in particular, for T4 endonuclease V (i.e., expression vectors capable of producing the protein at levels equal to or greater than 25% of cellular protein) have not existed in the art. Alterations in the amino acid sequence have failed to increase yield or activity of T4 endonuclease V. Similarly, alterations in the nucleotide sequence coding for T4 endonuclease V have not produced significantly increased yield or activity.

The real and perceived barriers to high expression and recovery of CPD glycosylases have been:

(1) The art has not recognized that nucleotide sequences for CPD glycosylases have been optimized by evolution for expression at low levels consistent with the other functions of the cell. For example, the denV gene sequence has been optimized by evolution for the fastest and highest level of expression only during the early phase of phage T4 infection and for shutdown thereafter.

(2) The art has erroneously believed that high levels of CPD glycosylases, e.g., T4 endonuclease V, cannot be achieved because supposedly such levels are lethal to the cell, e.g., *E. coli*.

(3) Proteins expressed at high levels typically form inclusion bodies, which are insoluble and inactive, and the art has not developed efficient and economical techniques for recovering activity from proteins in inclusion bodies, and, in particular, recovering DNA repair activity from CPD glycosylase proteins in inclusion bodies.

IV. SUMMARY OF THE INVENTION

For ease of presentation, the aspects of the invention relating to DNA coding will be discussed in terms of a set of "rules." Table 1 contains what are designated as "Prior Art Rules" since they have been previously employed to optimized DNA sequences for expression in, for example, *E. coli*.

Table 2 contains two groups of codons that are used in what will be referred to herein as the "Codon Selection Rules." The Codon Selection Rules state:

(1) in designing a recombinant CPD glycosylase gene for a CPD glycosylase protein, use at least one codon from Group A for more than 75% of the occurrences of the amino acid coded by the codon in the protein and at least one codon from Group B for more than 75% of the occurrences of the amino acid coded by the codon in the protein; and/or (2) in designing a recombinant CPD glycosylase gene for a CPD glycosylase protein, use at least two codons from Group A for more than 45% (preferably more than 75%) of the occurrences of the amino acid coded by the codon in the protein and at least two codons from Group B for more than 45% (preferably more than 75%) of the occurrences of the amino acid coded by the codon in the protein; and/or (3) in designing a recombinant CPD glycosylase gene for a CPD glycosylase protein, use at least three codons from Group A for more than 35% (preferably more than 45%, most preferably more than 75%) of the occurrences of the amino acid coded by the codon in the protein and at least three codons from Group B for more than 35% (preferably more than 45%, most preferably more than 75%) of the occurrences of the amino acid coded by the codon in the protein.

In certain preferred embodiments, both the Prior Art Rules and the Codon Selection Rules are used, with the Codon Selection Rules taking precedence over the Prior Art Rules in the case of a conflict between the two sets of rules.

In accordance with a first aspect, the invention thus provides an isolated, synthetic, and/or recombinant polynucleotide which employs the Codon Selection Rules. In particular the invention provides an isolated, synthetic, and/or recombinant polynucleotide comprising:

(a) a nucleotide sequence encoding a CPD glycosylase protein; and/or (b) a complement of the nucleotide sequence, wherein the complement and the nucleotide sequence consist of the same number of nucleotides and are 100% complementary;

wherein:

(I) Groups A and B represent the following codons for the following amino acids:

| Amino Acid | Codon |
|---|---|
| Group A | |
| Tyrosine | TAC |
| Glycine | GGT |
| Valine | GTT |
| Serine | TCT |
| Alanine | GCT or GCA |
| Group B | |
| Isoleucine | ATC |
| Phenylalanine | TTC |
| Aspartic Acid | GAG |
| Histidine | CAC | and (II) the nucleotide sequence comprises:

(a) at least one codon from Group A for more than 75% of the occurrences of the amino acid coded by the codon in the CPD glycosylase protein and at least one codon from Group B for more than 75% of the occurrences of the amino acid coded by the codon in the CPD glycosylase protein; and/or (b) at least two codons from Group A for more than 45% (preferably more than 75%) of the occurrences of the amino acid coded by the codon in the CPD glycosylase protein and at least two codons from Group B for more than 45% (preferably more than 75%) of the occurrences of the amino acid coded by the codon in the CPD glycosylase protein; and/or (c) at least three codons from Group A for more than 35% (preferably more than 45%, most preferably more than 75%) of the occurrences of the amino acid coded by the codon in the CPD glycosylase protein and at least three codons from Group B for more than 35% (preferably more than 45%, most preferably more than 75%) of the occurrences of the amino acid coded by the codon in the CPD glycosylase protein.

In accordance with a second aspect, the invention provides a cell comprising a CPD glycosylase protein wherein the CPD glycosylase protein comprises at least 25 weight percent of the total protein of the cell. In accordance with this aspect, the level of CPD glycosylase protein can be determined by obtaining a sample of a culture of the cells, washing the cells to remove the growth medium, and then determining the total protein content of the cells and the CPD glycosylase protein. Typically, the 25 weight percent level will be achieved towards the end of the fermentation process.

In the case of cells that are engineered to excrete the CPD glycosylase protein, the weight percent in the cells may be lower than in cells which retain the protein. In the case of such excreting cells (as well as cells that do not excrete or do not substantially excrete), the invention in accordance with a third aspect provides a culture of cells that produces a CPD glycosylase protein wherein for at least one period of at least ten minutes, at least 25 weight percent of the total protein produced by the culture during the period is the CPD glycosylase protein.

In accordance with a fourth aspect, the invention provides a method for producing a CPD glycosylase protein comprising:

(a) culturing cells which produce the CPD glycosylase protein; and (b) collecting the CPD glycosylase protein;

wherein the CPD glycosylase protein comprises at least 25 weight percent of the total protein produced by the cells during step (a).

In accordance with a fifth aspect, the invention provides a method for producing a protein (e.g., a CPD glycosylase protein) comprising:

(a) culturing cells which produce the protein, at least some of said protein being in inclusions bodies; and (b) collecting the protein;

wherein in step (b), at least part of the protein produced by the cells in step (a) is subjected to a mixing process that comprises: (i) forming two or more flowing streams at least one of which contains inclusion bodies which contain the protein, and (ii) impinging the streams on one another to disrupt at least some of the inclusion bodies.

In accordance with these aspects of the invention, the at least one flowing stream which contains the protein can contain intact cells, disrupted cells, or combinations thereof.

In certain embodiments of this aspect of the invention, at least one of the flowing streams has a velocity V1 prior to the impingement and the impingement produces a stream that has a velocity V2, where V1 minus V2 is greater than or equal to 90 meters/second. For example, at least one of the flowing streams can have a velocity greater than or equal to 100 meters/second (e.g., a velocity of at least 150 meters/second) prior to the impingement, and the impingement can produce a stream that has a velocity which is less than 10 meters/second (e.g., a velocity of approximately 1 meter/second). As a specific example, two flowing streams each having a velocity greater than or equal to 100 meters/second prior to the impingement can form a single stream as a result of the impingement that has a velocity which is less than 10 meters/second. Other stream configurations can be used as desired, e.g., the two or more flowing streams can form more than one stream after the impingement.

Although not wishing to be bound by any particular theory of operation, it is believed that stream mixing of a solution containing bacteria causes the bacteria to collide and break apart and in addition causes inclusion bodies of coagulated protein within the bacteria to also collide and break apart, resulting in solubilization of the protein contained in the inclusion bodies. If the bacteria are disrupted prior to stream mixing, the stream mixer no longer needs to break up the bacteria, but still serves to break up and thus solubilize the protein contained in inclusion bodies.

If the stream mixing is performed on intact cells, microscopic examination of the solution resulting from the mixing will preferably reveal no intact bacterial cells. As to inclusion bodies, if a solution produced by stream mixing is centrifuged to remove insoluble components, the supernatant will preferably contain at least 50% (more preferably at least 75%) of the protein contained in inclusion bodies prior to stream mixing. As a specific example, such centrifugation can be performed for 15 minutes using a Beckman Avanti J-20 centrifuge equipped with a JLA 8.1000 rotor and operating at 8,000 rpm, which produces 15,900×G, or with equivalent equipment.

The stream mixing aspects of the invention are preferably used with CPD glycosylases but can also be used with other proteins. Such other proteins preferably have molecular weights of less than 60,000 daltons, i.e., they contain less than about 600 amino acids. Such relatively small proteins have limited numbers of three dimensional configurations and thus when acted upon by the stream mixing process have a high likelihood of refolding into their native configuration. Enzymes are typical examples of such small proteins. As specific examples, stream mixing has been found to successfully recover active enzyme from inclusion bodies containing 8-oxoguanine glycosylase (OGG1), as well as inclusion bodies containing photolyase from Anacystis nidulans (see Example 6 below).

Additional features and advantages of the invention are set forth in the detailed description which follows, and in part will be readily apparent to those skilled in the art from that description or recognized by practicing the invention as described herein.

It is to be understood that both the foregoing general description and the following detailed description are merely exemplary of the invention, and are intended to provide an overview or framework for understanding the nature and character of the invention as it is claimed. Also, the above listed aspects of the invention, as well as the preferred and other embodiments of the invention discussed below, can be used separately or in any and all combinations.

The accompanying drawings are included to provide a further understanding of the invention, and are incorporated in and constitute a part of this specification. The drawings illustrate various embodiments of the invention, and together with the description serve to explain the principles and operation of the invention.

V. BRIEF DESCRIPTION OF THE DRAWINGS

FIGS. 1A and 1B show a comparison of native and recombinant denV gene sequences. For each segment of the gene, the amino acid sequence (SEQ ID NO: 2) is on the top row, the native gene sequence (SEQ ID NO: 3) is in the second row, the third row shows the changes in the sequence introduced by Inaoka (SEQ ID NO: 4), and the fourth row shows the changes in the gene sequence in accordance with the Prior Art Rules and the Codon Selection Rules of the present invention (SEQ ID NO: 1). FIG. 1A shows amino acids 1 through 80 and FIG. 1B shows amino acids 81-138 and the termination codon.

FIG. 2 shows a map of the pARAdenV expression vector. The map shows the recombinant denV gene downstream from the ARA promoter and upstream of the strong terminator rrnB1. The vector (plasmid) also contains the kanamycin resistance gene for selection and the pUC18 origin of replication.

VI. DETAILED DESCRIPTION OF THE INVENTION AND ITS PREFERRED EMBODIMENTS

A. The CPD Glycosylase Family and Subfamilies

All the members of the CPD glycosylase family share the same unique activity in the DNA repair process, but they can be separated into two subfamilies based on their amino acid sequence homology relative to one or the other of two archetypal enzymes: T4 endonuclease V and *Micrococcus luteus* UV endonuclease. The members of the family and subfamilies are not as easily recognized by comparing the nucleotide sequences because of the degeneracy of the genetic code; i.e., an organism's preference for A-T or G-C base pairing in the third position of the codon significantly distorts the nucleic acid sequence similarities even when the amino acid sequences are quite similar.

The first subfamily, which is closely related to T4 endonuclease V, includes the CPD glycosylases from the following organisms and their related strains: Bacteriophage RB69, *Paramecium bursaria Chlorella* virus 1, *Prochlorus marinus, Bordetella parapertussis, Haemophilus ducreyi, Brucella melitensis* and *Pasteurella multocida*. The second subfamily, which is more closely related to *Micrococcus luteus* UV endonuclease, includes the CPD glycosylases from the following organisms and their related strains: *Nitrosomonas europeaea* and *Azoarcus* sp. EbN1.

The similarity to one or the other of the archetypal CPD glycosylases can be determined by aligning the amino acid sequences. The homologies are not exact, and gaps are therefore introduced to align the amino acid sequences. For clarity in discussing amino acid sequence homologies and similarities,. the amino acids for both subfamilies are numbered based on the T4 endonuclease V archetypal sequence. For example, homology at amino acid 17 refers to the $17^{th}$ amino acid in the T4 endonuclease V sequence, although it may actually be the $16^{th}$ or the $18^{th}$ or some other amino acid in a particular protein sequence of either subfamily.

The alignment may be performed manually, but it is preferably performed by computational analysis, using, for example the Smith-Waterman algorithm (Waterman 1995).

In general, the aligned sequences of the CPD glycosylases show more homology at the amino and carboxy ends than in the middle of the protein. The homology between the two archetypes of the CPD glycosylases, T4 endonuclease V and *Micrococcus luteus* UV endonuclease, is 27% (31 of 115 possible amino acid matches). As for the specific homologies between the archetypal CPD glycosylases, it should be noted that four amino acid residues previously proposed as functionally important in the T4 endonuclease V enzyme (Arginine at position 3, Arginine at position 22, Glutamic acid at position 23 and Lysine at position 121) are all conserved in the *Micrococcus luteus* sequence (Shiota and Nakayama, 1997).

The members of the first subfamily, homologous with archetypal T4 endonuclease V, share homology at the 8 amino acids shown in Table 3, some of which have been associated with the biological activity of the protein. In addition, the family shares a sequence similarity between amino acids 115 and 121, which is a region thought to be important for substrate binding. Although the sequence is not identical for all members of the subfamily, the choice of amino acids at each position is usually between two, or, in one case, among four. The sequence is described in Table 4, second column.

The second subfamily, homologous with archetypal *M. luteus* UV endonuclease, also shows a sequence similar to the first group between amino acids 116 and 123. See the third column of Table 4. As can also be seen in this table, the two subfamilies have homology or similarity at amino acid positions 116, 118, 119, and 121.

The CPD glycosylase which has the least homology to its archetypal enzyme is from *Pasteurella*, which nevertheless shares 36% (50 of 138) amino acids with T4 endonuclease V. In particular, it shares the 8 conserved amino acids of the T4 endonuclease V subfamily listed in Table 3. Thus, in general, CPD glycosylases are proteins which, after alignment, share at least 35% homology with either the T4 endonuclease V archetype or the *M. luteus* archetype.

B. Codon Usage in Native CPD Glycosylase Genes

In accordance with the invention, a set of aversions (negative preferences) regarding codon usage for certain amino acids has been discovered in the native genes for the CPD glycosylases. In particular, nine amino acid codons, divided into two groups, are subject to these aversions: Group A consisting of tyrosine, glycine, valine, serine and alanine, and Group B consisting of isoleucine, phenylalanine, aspartic acid and histidine. For these amino acids, nature has an aversion for using a codon from Group A and a codon from Group B for more than 75% of the occurrences of those amino acids.

The codon usage for these nine amino acids for all of the known CPD glycosylase genes is shown in Table 5. In the instance of some of the CPD glycosylase genes, such as the CPD glycosylase gene from phage RB69, at least one codon from Group A is used more than 75% of the instances of that amino acid, but no codon from Group B is used at more than that frequency. In other cases, such as the CPD glycosylase gene from *Micrococcus luteus*, none of the codons from Group A are used over 75% of the instances of that amino acid, but at least one codon from Group B is used over 75% of the instances of that amino acid.

It is impossible to know why nature has developed these aversions, but based on the present invention, one might speculate that they evolved as a mechanism to limit efficient translation of the transcript of CPD glycosylase genes so that this protein does not become an unnecessarily large portion of the total protein of a cell.

C. Codon Selection Rules

As discussed above in the Summary of the Invention, in accordance with certain aspects of the invention, it has been discovered that codon usage for CPD glycosylases should follow at least one of three Codon Selection Rules, namely:

(1) in designing a recombinant CPD glycosylase gene for a CPD glycosylase protein, use at least one codon from Group A for more than 75% of the occurrences of the amino acid coded by the codon in the protein and at least one codon from Group B for more than 75% of the occurrences of the amino acid coded by the codon in the protein; and/or (2) in designing a recombinant CPD glycosylase gene for a CPD glycosylase protein, use at least two codons from Group A for more than 45% (preferably more than 75%) of the occurrences of the amino acid coded by the codon in the protein and at least two codons from Group B for more than 45% (preferably more than 75%) of the occurrences of the amino acid coded by the codon in the protein; and/or (3) in designing a recombinant CPD glycosylase gene for a CPD glycosylase protein, use at least three codons from Group A for more than 35% (preferably more than 45%, most preferably more than 75%) of the occurrences of the amino acid coded by the codon in the protein and at least three codons from Group B for more than 35% (preferably more than 45%, most preferably more than 75%) of the occurrences of the amino acid coded by the codon in the protein.

The use of these Codon Selection Rules has been found to result in expression of polynucleotide sequences for CPD glycosylases at levels that are useful for commercial production.

Certain embodiments of the invention follow the approach of designing a recombinant CPD glycosylase gene for a CPD glycosylase protein by using all codons from Groups A and B for more than 35% (preferably more than 45%, most preferably more than 75%) of the occurrences of the amino acid coded by the codon in the protein.

These approaches to codon selection ameliorate the limitations on expression of CPD glycosylases resulting from the evolutionary optimization of the nucleotide sequences for these proteins that has resulted in expression at low levels consistent with the other functions of the cell.

D. Prior Art Rules

The art has developed rules for modifying codons in exogenous genes to optimize expression in *E. coli*, an example of which is the Primo 3.4 program available from Chang Bioscience, Inc. The preferred codon usage rules of the prior art for *E. coli* are shown in Table 1. Similar rules exist for other hosts.

The present invention makes use of these prior art rules, except where they conflict with the Codon Selection Rules of the invention. In the cases of conflict, the Codon Selection Rules of the invention take precedence, unless those rules would lead to tandem duplication of a codon in which case the prior art rule will be used to avoid such a tandem duplication (see, for example, amino acid 131 of FIG. 1B).

E. Application of the Codon Selection Rules to the Native denV Gene and Other CPD Glycosylases In certain of its preferred embodiments, the present invention relates to methods for preparing a recombinant version of the nucleotide sequence for a CPD glycosylase protein, e.g., the native denV gene, without altering the amino acid sequence.

FIG. 1 shows a specific application of these embodiments to the T4 endonuclease V enzyme, which is currently a DNA repair enzyme commercially sold and widely used. In particular, this figure shows the nucleotide sequences of the native denV gene (SEQ ID NO: 3) and a recombinant denV gene designed in accordance with the Prior Art Rules (SEQ ID NO: 4) and the Codon Selection Rules of the invention (SEQ ID NO: 1). The amino acid sequence of T4 endonuclease V (SEQ ID NO: 2) is also shown, and this is unchanged by the coding of the recombinant gene. In particular, amino acid 129 is tyrosine and is not changed as described in U.S. Pat. No. 5,308,762.

The changes in the recombinant gene (SEQ ID NO: 1) are shown in FIG. 1 on the line marked "AGI". These changes are contrasted with the changes made in the synthetic denV gene (SEQ ID NO: 4) of Inaoka (shown on the line marked "Inaoka"). It is clear that the AGI and Inaoka genes (SEQ ID NO: 1 and SEQ ID NO: 4) share very few changes. This is because the Inaoka changes were made for purposes of introducing restriction sites in the nucleotide sequence, and the AGI changes of the present invention were made for enhancing gene expression.

In designing the recombinant denV gene sequence, special conditions of phage T4 gene expression were considered. When phage T4 infects a cell, it destroys the *E. coli* tRNA that pairs to the CTG codon for leucine translation. This infection tactic reduces the transcription of host genes. The phage T4 genes avoid this problem by using alternate codons for leucine, such as TTA or TTG. In addition, when phage T4 infects a cell, it produces tRNA for codons in low abundance in *E. coli* and it also includes these rarely used codons in the denV gene. This infection tactic serves to divert translation to phage-specific proteins such as T4 endonuclease V. However, in the situation of the native denV gene expressed from a plasmid, translation of these rarely used codons without the supplemental phage tRNAs for these codons is suboptimal.

In Table 6 the codon usage in the native T4 endonuclease V gene is contrasted with the most preferred codon usage directed by the present invention in the recombinant T4 endonuclease V gene. As can be seen in this table, in accordance with the most preferred embodiments of the invention, codon usage has been changed so that codons from Group A are used more than 75% of the time, and in addition codons from Group B are also used more than 75% of the time.

Overall, 71 of the 138 amino acid codons are changed in the native denV gene sequence by either the rules of the prior art or those of the present invention. Of these 71 changes, 36 changes are different between the rules of the invention and those of the prior art.

The present invention also directs the use of codons that differ from the native sequence or those instructed by the prior art when the denV gene is expressed in other hosts, such as yeast or the plant *Arabidopsis*. That is, the Codon Selection Rules described above apply equally when the denV gene is expressed in hosts other than *E. coli*.

Similarly, the present invention directs the use of codons that differ from the native sequence or those instructed by the prior art when other DNA repair genes, such as the *E. coli* ada gene for repair of $O^6$-methylguanine, or the *Arabidopsis* OGG1 gene for repair of 8-oxo-guanine, is expressed in *E. coli* or in other hosts. Again, the Codon Selection Rules described above are applied for these other protein/host combinations.

Thus the rules of the present invention provide general guidance for the use of different and non-obvious codons in designing genes for enhanced expression of a variety of DNA repair genes in a variety of hosts.

For any given DNA repair enzyme, or more specifically any CPD glycosylase, the protein, and thus its DNA sequence, may be shortened or truncated to increase its stability without changing its enzymatic specificity, or it may contain within the final protein the full length of the native amino acid sequence. For example, the protein may be truncated to remove the endonuclease, or β-elimination, activity, since this activity may be provided by either other non-DNA-damage specific enzymes or by non-enzymatic cleavage of the DNA. The CPD glycosylase may be grafted to or combined with another protein to form a chimera with added binding specificity and/or specificities, or to bring two or more activities closer together in space. Additional amino acids or other modifications may be added to direct localization to the nucleus, mitochondria, or other organelles in order to direct DNA repair to these sites. Additional amino acids or other modifications may be added to the protein to simplify purification, such as adding a peptide sequence that binds with high affinity to a ligand that can be attached to a solid support. The present invention includes these and other changes to the amino acid sequences for CPD glycosylases and nucleotide sequences coding for those proteins, now known or subsequently develoned.

F. Expression Systems

Other than for the Codon Selection Rules discussed above, nucleic acid synthesis, cloning, and expression of the CPD glycosylases follows standard/conventional techniques now known or subsequently developed in the art. Extensive reviews of such techniques can be found in such texts as *Molecular Cloning: A Laboratory Manual*, vol. I-III (eds. J. Sambrook, E. F. Fritsch, T. Maniatis), 1989.

For example, in the case of the recombinant denV gene, the recombinant nucleotide sequence can be placed adjacent to and under the control of an *E. coli* promoter. The promoter and structural gene can then be cloned into a plasmid with a selectable marker so that only bacteria with the intact plasmid grow in the fermentation conditions.

Any suitable host may be used, as long as the promoter for the recombinant sequence is compatible with the host transcription and translation metabolism. Some host strains may be found to express the gene more efficiently than do others (see, for example, Example 2 below).

Many types of media may also be used for fermentation of the host, including minimal media with defined components and enriched media containing extracts of yeast and digested proteins. The expression vectors may be induced by addition of the appropriate inducing agent, which can be a chemical, such as isopropylthiogalactoside or L-arabinose, or a change in physical conditions, such as temperature or dissolved oxygen. The inducer may be present during all phases of growth, or it may be added after the culture has progressed to a desired phase of growth.

The particular conditions to be used for any particular CPD glycosylase/host combination can be readily determined from the current disclosure and the general knowledge in the art of genetic engineering.

G. Determination of Levels of Protein Production

The protein production of a culture of cells may be determined by various techniques known in the art. For example, protein production can be determined by sampling the culture at intervals of, for example, 10 minutes during fermentation, and subjecting the proteins in the sample to SDS-polyacrylamide gel electrophoresis, followed by staining with Coomassie. The fraction of CPD gJycosylase in total cell protein can be determined by, for example, densitometry scanning of the stained gel. The total cell protein can be determined by, for example, summing the densities of all the bands (subtracting out any bands contributed by the media, which is determined from a lane loaded with media alone in the gel). The identity of the CPD glycosylase band can, for example, be determined by including in the gel a standard of purified CPD glycosylase, and the CPD glycosylase amount can be determined by, for example, the density of its band. For each time point sample, the fraction of total protein can be determined by, for example, dividing the density of the CPD glycosylase band by the sum of the densities of the total cell proteins. The rate of protein production by percent of total protein can be determined by, for example, comparing the results from two samples collected 10 minutes apart and calculating the change in the density of the CPD glycosylase band density divided by the change in the sum of the densities of the total cell protein. The resulting fraction times 100 is then the weight percent of the CPD glycosylase protein produced by the culture during the 10 minute period relative to the total protein produced by the culture during that period.

As another alternative, the percentage of protein synthesis during a 10 minute period that is CPD glycosylase synthesis can also be determined by the "pulse-chase" labeling technique, which is well known to protein chemists. In this protocol, a cell sample is exposed to a radio-labeled amino acid for ten minutes (the "pulse"). The labeled amino acid is one which is present in essentially all protein, such as $^{35}$S-methionine. The cells are washed with a buffer solution to remove the isotope, and finally incubated with a unlabeled amino acid (the "chase"), for an additional 10 minutes. The cells are collected and the proteins separated by SDS-polyacrylamide gel electrophoresis. The gel is imaged using X-ray film or a phosphorescence imager, and all the proteins that were made during the 10 minute pulse period appear in the image because of the radio-label. The intensity of the CPD glycosylase band divided by the intensity of the sum of all the proteins is the percentage of protein synthesis during a 10 minute period that is CPD glycosylase.

H. Recovery of CPD Glycosylase Activity

Following fermentation, the cells may be collected from the cell culture media by any of several methods, including fixed voliume, or continuous flow centrifugation, or filtration. The cells to be processed may be in a form of a dry power produced by lyophilization, or as a moist powder referred to as paste. The cells may then be dispersed in liquid at a concentration of between, for example, 5 and 500 grams per liter, and the liquid may be any suitable buffer or water. The mechanism of dispersion may be by many methods, including an overhead mixer with a paddle or marine impeller, and the duration of mixing may be, for example, 30 minutes or longer at, for example, refrigerated to room temperature. In cases of cells that are expected to be particularly difficult to disrupt, the dispersion process can include methods to enhance subsequent cell lysis, such as adding to the dispersion medium a lysing agent like lyoszyme.

Alternatively, an expression vector in combination with an appropriate host can be used whereby the highly expressed protein is secreted out of the cells and into the media. In this case, recovery of the protein simply involves removal of the cells and collection of the culture media.

High levels of protein expression often lead to the formation of inclusion bodies. Such bodies may be contained within the host cells and/or may be found in the culture medium. Many methods have been used to recover protein and/or protein activity from inclusion bodies, but all of these methods, e.g., those methods which use high concentrations of guanidine chloride, produce denatured protein as an intermediate. As a result, recovery of protein and/or activity from inclusion bodies has required an additional step of removal of the denaturing agent in order to allow refolding of the protein. In accordance with certain aspects of the invention, it has been unexpectedly found that stream mixing homogenizes (solubilizes) the inclusion bodies of T4 endonuclease V and other proteins without the use of a denaturing agent and results in soluble and active protein. In particular, the cell suspension may be homogenized by methods that include forcing an impingement (collision) between two streams of dispersed cells each flowing at a velocity greater than 150 meters/second so as to produce a single resultant stream that is flowing at about 1 meter/second. After homogenization the lysate may be clarified by many methods such as centrifugation or filtration.

Example 3 and Table 7 compare T4 endonuclease V in a water-based SUneerratant nrepared using the same cell paste and either a standard method of sonication or the method of stream mixing described herein. The first data column in Table 7 shows the results from the sonication processing and the second column shows the results from the stream mixing process. The third column shows the ratio of the results from stream mixing divided by sonication. The total amount of protein per milliliter recovered from the stream mixing approach was more than double the amount recovered from sonication. Analysis of the undissolved precipitate from the sonication process by both SDS-PAGE and Western blot revealed that a substantial amount of T4 endonuclease V remained insoluble. This is characteristic of undissolved inclusion bodies. The total concentration of T4 endonuclease V in the soluble fraction of the stream mixed sample was more than seven-times greater than in the sonicated sample. This value is greater than the increase in total protein concentration, indicating that the stream mixing step selectively solubilized the T4 endonuclease V. The result was a doubling of overall purity.

The recovered protein was biologically active. The unit activity, which is a measurement of biological activity per unit volume, was determined using the procedures of Example 1 of the U.S. Pat. No. '211 patent. This value increased 5-fold, indicating that the stream mixing process not only increased the yield of protein but that the protein was also active. The specific activity, which is the unit activity divided by the amount of protein in micrograms, was twice as great, reflecting the increase in purity.

Although stream mixing is a preferred approach for the recovery of CPD glycosylase protein and activity, the present invention does not require the use of this procedure. For example, techniques which involve the use of solubilizing agents which denature the CPD glycosylase can be used if desired. See, for example, Yarosh et al., 1999.

After stream mixing (if used), the CPD glycosylase may be recovered by various purification techniques now known or subsequently developed in the art, including, without limitation, affinity chromatography, size exclusion chromatography, ion-exchange chromatography, and combinations of these or other methods. Standard and conventional methods of protein purification are covered in many text books, including Scopes, 1994. The goal of the purification is to reach a CPD glycosylase purity which is preferably 95% or greater.

A significant problem in commercial scale purification of T4 endonuclease V is the presence of contaminating HUα proteins. These are abundant proteins in E. coli and have many characteristics similar to T4 endonuclease V so that they co-purify using industrial separation methods. The proteins may be separated using research-scale techniques, but these methods result in greatly reduced yield of T4 endonuclease V. This may not be a concern for a research program that requires small amounts of very pure protein, but it is unsatisfactory for a commercial scale production scheme that requires large amounts of protein, e.g., amounts suitable for regulatory approval. Similar purification problems can exist for other CPD glycosylases based on the endogenous proteins of the host cell.

Example 4 and Table 8 show the results of a commercial-type purification scheme applied to E. coli cultures expressing either the native or recombinant denV gene. The purification steps were the same for the two cultures. In particular, the cell paste for each was sonicated and then purified following the methods of the U.S. Pat. No. '211 patent. The first data column in Table 8 reports the overall protein yield and the second column reports the yield of T4 endonuclease V determined by Western blotting. The third column reports the purity of the preparation, which is the yield of T4 endonuclease V divided by the total protein yield.

As can be seen from this data, the recombinant gene expression system produced more protein than the native gene expression system. Specifically, the yield of T4 endonuclease was over 60-fold greater for the recombinant system, resulting in a lysate which was 36% pure compared to not even 1% pure in the case of the native gene protein. At each step of purification, the purity of the recombinant gene protein preparation was substantially greater, being nearly homogenous following gel filtration.

The final preparation of T4 endonuclease V from the native gene expression system contained approximately 20% of its protein as HUα, which was clearly visible in SDS-PAGE gels loaded with as little as 2.5 micrograms of protein (data not shown). The final preparation of T4 endonuclease V from the recombinant gene expression system, on the other hand, was virtually completely pure, and no HUα protein was visible in gels loaded with 5 micrograms of protein (data not shown). HPLC analysis of these preparations confirmed that HUα was detectable in native gene expressed protein but unrdetectable in recombinant gene expressed protein. An explanation for this is that the increased yield of T4 endonuclease produced a much higher ratio of endonuclease to HUα protein. Therefore, when a few micrograms of total protein were analyzed, the HUα fraction was so greatly reduced as to be undetectable.

I. Topical Preparations

CPD glycosylases can be administered in various ways, a preferred form of administration being topical since sun damage to DNA of the skin is prevalent and the resulting cancers are a serious health concern. In order to achieve delivery into the skin, the proteins may be formulated in many forms, which include delivery vehicles such as liposomes, microsponges or nanoparticles, and which may include penetration enhancers such as oleic acid.

Liposomes may be dispersed in many types of formulations, including hydrogel formulations. Many types of hydrogels are available and they may be used at between 0.5% and 1%. However, the important factor is not the concentration of the hydrogel, but the viscosity of the resulting formulation. For example, using a salt buffer such as phosphate buffered saline, a 1% formulation of the hydrogel Hypan SS201 has a viscosity of only about 200 centipoises, while a 1% formulation of the hydrogel Carbomer 981 NF produces a lotion with a viscosity of over 3,000 centipoises.

The liposomes may be combined with other ingredients that benefit the skin, such as sunscreens, anti-oxidants, moisturizers, anti-inflammatory or anti-nociceptic agents, fragrances, colors and other ingredients used in the art. They may also be combined with excipients that increase the stability of the formulation or its ingredients, and with preservatives that prevent microbial contamination.

A surfactant in the lotion at sufficiently low concentration can improve the tactile feel of the lotion without disrupting the liposomes. Many types of surfactants may be used, including many grades of polyethylene glycol (PEG), also called CARBOWAX. Concentrations are preferably in the range of 1% to 10%, e.g., approximately 5%. Surfactants may be used with water-insoluble ingredients, such as oils and chemical sunscreens, to produce emulsions. The emulsions may be characterized as oil-in-water, water-in-oil, or water-in-oil-in-water An example of a suitable formulation for topical administration is discussed in Example 5. This example includes procedures which result in a lotion that has the tvne of "feel" that people expect from a topical product that should be used often, e.g., every day, to prevent DNA damage caused by sun exposure.

Although patients with life threatening skin diseases such as xeroderma pigmentosum may be willing to use less appealing formulations, compliance for patients with less serious disease requires a more attractive formulation, such as that of Example 5. People who benefit from such a formulation include patients whose DNA repair has been impaired by the use of immunosuppressive drugs, such as cyclosporine A, tacrolimus, picrolimus, ascomycin, FK506 and other calcineurin inhibitors, and rapamycin and other cyclophilin binding drugs. Other people who benefit from a formulation with a good "feel" are those with latent Herpes labialis infections who are at risk for reactivation of the virus due to sun exposure. Still another group of people who benefit from such a formulation are those with autoimmune disease or photosensitive diseases that are exacerbated by DNA damage from UV light exposure, such as lupus erythematosus and polymorphic light eruption.

Without intending to limit it in any manner, the present invention will be more fully described by the following examples.

EXAMPLE 1

Synthesis of Recombinant T4 denV Gene

A recombinant T4 denV gene was synthesized as single-stranded pieces using the Codon Selection Rules and the Prior Art Rules discussed above for each occurrence of each amino acid to which the rules apply. The pieces were annealed to complementary strands with unique overhangs, the double-stranded pieces comprising the structural gene were then annealed and the full gene assembled by ligation.

FIG. 1 shows the nucleotide sequence of the native and recombinant denV genes. In each row, the top line shows the T4 endonuclease V amino acids using three-letter designations (SEQ ID NO: 2). The second line begins with the codon/amino acid number, and then the native denV gene nucleotide sequence (SEQ ID NO: 3). The third line shows the nucleotide changes in the synthetic gene constructed by Inaoka (SEQ ID NO: 4). The fourth line shows the nucleotide changes in the recombinant gene of the present invention, designated AGI (SEQ ID NO: 1). Finally, in the second to the last row, the amino acid substitution of U.S. Pat. No. 5,308,762 is shown.

The nucleotide sequence designated as AGI in FIG. 1 is SEQ ID NO:1. As discussed above, this sequence is the nucleotide sequence of the denV gene modified by the Codon Selection Rules and the Prior Art Rules.

EXAMPLE 2

Construction of the pARA denV Plasmid

The structure of the expression plasmid used to produce T4 endonuclease V enzyme is shown in FIG. 2.

The recombinant denV gene of Example 1 was cloned into the KpnI site of the pBAD plasmid just downstream from the E. coli araB (or ara-2) promoter and upstream of the strong terminator rniB 1. The pBAD plasmid is available from Invitrogen Corporation, 1600 Faraday Avenue, PO Box 6482, Carlsbad, Calif. 92008, and contains the kanamycin resistance gene for selection and the pUC18 origin of replication. This construct was called pARAdenV.

The plasmid was transformed into competent cells of the E. coli host strain LMG194, which was found to produce more T4 endonuclease V than the strain KS272, using the calcium chloride precipitation technique. The LMG194 E. coli strain is available from Invitrogen Corporation, 1600 Faraday Avenue, PO Box 6482, Carlsbad, Calif. 92008. Transformed colonies were selected on LB plates containing kanamycin. The selected colonies were cultured in M9 media, containing a mixture of salts, casamino acids and glycerol, wherein they produced more T4 endonuclease V than when grown in LB media, containing tryptone, yeast extract and salt, or HSP-A media, containing soy protein, yeast extract and salt.

A master cell bank of vials containing aliquots of the transformed cells was prepared, and validated by sequencing the plasmid from one of the master bank vials. A working cell bank was prepared by expansion of one vial of the master cell bank, and this bank was used to inoculate fermentation batches. The stability of the plasmid in the E. coli was verified by comparing colony counts on plates with and without kanamycin. The similarity of the counts demonstrated that >95% of the cells in the working cell bank contained the plasmid.

This plasmid, i.e., the pARA denV plasmid of FIG. 2, has been deposited with the American Type Culture Collection, 10801 University Boulevard, Manassas, Va., 20110-2209, United States of America, in E. coli strain LMG194 and has been assigned the accession number PTA-6785. This deposit was made under the Budapest Treaty on the International Recognition of the Deposit of Micro-organisms for the Purposes of Patent Procedure (1977) on Jun. 13, 2005.

The transformed cells were induced to express T4 endonuclease V with arabinose in several ways, including, at one extreme, treatment of a high density culture with about 0.3% L-arabinose for a few hours at 37° C., and, at the other extreme, treatment of a low density culture with a concentration of about 0.001% L-arabinose for several hours at 25° C. The most practical method with the best yield was found to be addition of 0.003% L-arabinose to the inoculated culture at 37° C., i.e., a low density culture, followed by growth to a high density, stationary phase before harvesting the cells.

EXAMPLE 3

Enhanced Recovery of CPD Glycosylase Activity

Induction of expression of recombinant T4 endonuclease V using the plasmid of Example 2 was found to result in accumulation of the expressed protein in the insoluble fraction of a sonicated lysate, which is characteristic of inclusion bodies.

Specifically, from 2 h to 8 h post-induction, the proportion of the soluble protein fraction that was T4 endonuclease V remained at about 10-20% of total protein, while the fraction of insoluble protein that was T4 endonuclease V dramatically increased from 25% to over 70%. Overnight incubation of these cultures resulted in a yield of about 40% protein in the soluble fraction as T4 endonuclease V, while in the insoluble fraction the proportion was over 90%.

Following fermentation, the cells were collected by fixed volume centrifugation, and processed to a dry power by lyophilization. The cells were then dispersed at a concentration of about 76 grams per liter in a buffer of Phosphate Buffered Saline (PBS, 10 mM $NaHPO_4$, 150 mM NaCl, pH 8) with 0.1% Triton X-100 using an overhead mixer with a paddle or marine impeller, with overnight mixing at refrigerated temperature. In some cases of cells that were particularly difficult to disrupt, 1 volume of cold water and Triton X-100 was added to a final concentration of 0.25% (v/v).

The cell suspension was processed using a stream mixer, specifically, a Model M-110Y Microfluidize® (Microfuidics Inc., Newton, Mass.). This device is equipped with two chambers: the H30Z Auxiliary Processing Module (APM), which has a nominal passage size of 200 microns and the H10Z Interaction Chamber (IC), which has a nominal passage size of 100 microns. The IC includes a Y-shaped chamber in which two streams interact (collide) at an angle to produce a single stream. The velocity of the two streams before collision is greater than 150 meters/second and after collision is about 1 meter/second. Although not wishing to be bound by any theory of operation, it is believed that kinetic energy is transferred to the cells in connection with this change in velocity which disrupts the cells and the inclusion bodies contained within the cells. The disruption of the inclusion bodies is believed to denature the protein so that it can subsequently refold into active protein.

When a single pass was performed, the product stream passed through both the APM and the IC. The operating pressure, in this case, was between 17,000 -20,000 psi at the start of processing, and leveled off to 12,000 -14,000 psi with further operation. When two passes were performed, the first pass was through the APM, which broke up the suspension. The suspension was then diluted with 2 volumes of PBS to prevent clogging, and then a second pass was performed through the APM and IC. In either case, the Microfluidizero® base and product outlet cooling coil were packed in ice during cell disruption in order to prevent the generation of degradation products.

After a single pass, no intact cells were apparent by microscopic examination. Accordingly, this approach is preferred since it involves fewer processing steps. After the completion of the stream mixing procedure, the debris in the solution was removed by centrifugation at 8,000 rpm for 15 minutes in a Beckman Model J2-21 centrifuge with a JA-10 rotor, followed by lysate clarification by filtration through 0.2 µm Sartobran P filters.

The stream mixing approach of the present invention was compared to a method of the prior art which used only sonication to lyse the cells. Cell paste from the recombinant expression vector induced with L-arabinose was prepared at approximately 40 grams per liter at refrigerated temperatures and was processed by sonication for 3 hours using a Misonix XL2020 Continuous Flow Sonicator (Farmingdale, N.Y.) at an output setting of 6. The paste reservoir was cooled with ice packs and circulated with a Cole Palmer Model 7591-50 peristaltic pump, Model 7019-21 pump head, with ⅜" i.d. tubing at setting number 5. Debris was removed by centrifugation at 6,800 rpm for 15 minutes using a Beckman Model JA-20 centrifuge with a JLA 8.1000 rotor.

The supernatants from the stream mixer (single pass procedure) and sonicator preparations were analyzed for (a) recovery of total protein, (b) T4 endonuclease V protein by Western blotting, and (c) DNA repair activity. Table 7 shows results for sonication (average of five preparations) and stream mixing (average of 2 preparations).

As can be seen in this table, the stream mixing method is clearly superior in yield of total protein (250%), and even more so in yield of T4 endonuclease V (710%). Total activity in the preparation (unit activity) is dramatically increased, due to the solubilization and reactivation of the T4 endonuclease V from the inclusion bodies. The protein purity is more than twice as great, and the specific activity (enzyme activity divided by total protein) is also twice as great, indicating that the protein contributing to the increased purity is also enzymatically active.

EXAMPLE 4

Comparison of Yield and Purity of T4 Endonuclease V Protein Purified from *E. coli* Cultures Expressing either the Native or Recombinant denV Gene Sequence

*E. coli* were induced to express either the native denV gene or the recombinant denV gene of Example 1 under the same conditions. In each case the T4 endonuclease V was purified by the same methods, i.e., the methods of the U.S. Pat. Nos. '211 and '231 patents. Table 8 compares the yield and purity of the preparations at each step in the production/purification process.

As can be easily observed in Table 8, at each step in the process, the T4 endonuclease V purity is greater in the preparation that began with the recombinant gene compared to expression from the native sequence. In the end, the native sequence method yielded protein with only 76% purity, while the recombinant gene yielded protein with 99% purity.

EXAMPLE 5

Topical Application of CPD Glycosylases

An example of a formulation that can be used to topically administer CPD glycosylases is shown in Table 9. In this table, the ingredients used in the formulation are followed by procedure steps which ensure that the lotion has a consistency and feel appropriate for daily topical administration.

EXAMPLE 6

Use of Stream Mixing to Recover Non-CPD Glycosylase Proteins

This example illustrates the use of stream mixing to recover proteins other than CPD glycosylases from inclusion bodies.

In a first experiment, photolyase from Anacystis nidulans was recovered from inclusion bodies formed in *E. coli* bacteria. Photolyase is a DNA repair enzyme having a molecular weight of 53 kd.

In this experiment, a cell paste of *E. coli* bacteria containing this photolyase in inclusion bodies was resuspended with gentle stirring overnight in phosphate buffered saline. The cell suspension was processed by stream mixing using a Microfluidics Model M-110Y pressure homogenizer with an H10Z interaction chamber at 2 to 8° C. The recovered homogenate was clarified by ultrafiltration and 0.2 µm filtration, which eliminated cells, cell debris and residual inclusion bodies. The recovered solution was further purified by quaternary ammonium membrane ion exchange chromatography.

The partially purified enzyme had a protein concentration of 0.31 mg/mL and a potency of 70 units per microgram, where a unit is defined as the number of endonuclease-sensitive sites per million bases removed per microgram of protein under standard assay conditions (Yarosh et al., 2002. ).

In a second experiment, 8-oxoguanine glycosylase (OGG1) from Arabidopsis thalania was recovered from inclusion bodies in *E. coli*. OGG1 is a DNA repair enzyme of 43 kd.

In this experiment, a cell paste of *E. coli* bacteria containing OGG1 in inclusion bodies was resuspended with gentle stirring overnight in a HEPES based buffer (50 mM HEPES, 10 mM NaCl, 10 mM EDTA, pH 8.0) at a density of 40 gm/L. The cell suspension was processed by stream mixing using a Microfluidics Model M-110Y pressure homogenizer with an H10Z interaction chamber at 2 to 8° C. The recovered homogenate was clarified by centrifugation and 0.2 µm filtration, which eliminated cells, cell debris and residual inclusion bodies. The recovered solution had a protein concentration of 16.45 mg/mL with an enzyme activity of $7.8 \times 10^2$ units per microgram, where a unit is defined as in the U.S. Pat. No. '211 patent.

In this example, as well as in Example 3, stream mixing was performed using a pressure homogenizer from Microfluidics Inc., Newton, Mass. Suitable equipment for performing stream mixing is available from various other manufacturers. For example, another device that causes stream mixing is the Emulsiflex-C50 made by Avestin Inc., 2450 Don Reid Drive, Ottawa, Canada. This device operates essentially like the Microfluidics device in that it spits the main stream into two streams which then collide with each other. A further device that causes stream mixing is the Mini DeBee, made by Bee International Inc., 46 Eastman Street, South Easton, Mass., which directs a first stream against a fixed surface, which rebounds and collides with the oncoming stream to cause the stream mixing. These or other devices now known or subsequently developed can be used in the practice of the stream mixing aspects of the invention.

As the foregoing examples demonstrate, in accordance with the invention, it has been unexpectedly found that changing the nucleotide sequence of the denV gene greatly increases the percentage of cell protein found as T4 endonuclease V, and without cell death. For the first time, cells have been prepared that consistently include much greater than 25% of cellular protein as T4 endonuclease V. It has been further unexpectedly discovered that, although a large fraction of the T4 endonuclease V in the cells so induced are in inclusion bodies, the use of a stream mixer solubilizes the inclusion bodies and recovers active protein. In this way, the two-step process of (a) solubilizing inclusion bodies using a denaturing agent and (b) subsequently removing the denaturing agent to obtain active protein can be avoided. The recombinant DNA aspects of the invention can be used with CPD glycosylases other than T4 endonuclease V, and the stream mixing aspects can be used with a variety of proteins other than CPD glycosylases.

Although specific embodiments of the invention have been described and illustrated, it will be apparent to those skilled in the art that modifications and variations can be made without departing from the invention's spirit and scope. The following claims are thus intended to cover the specific embodiments set forth herein as well as such modifications, variations, and equivalents.

LITERATURE REFERENCES

Atkins Latham, K. and R. S. Lloyd. T4 Endonuclease V. Perspectives on Catalysis. In *DNA Damage-Effects on DNA Structure and Protein Recognition*. Annals of New York Academy of Science, volume 726, 1994. pp181-197.

Augustine, M. L., R. W. Hamilton, M. L. Dodson and R. S. Lloyd. Oligonucleotide Site Directed Mutagenesis of All Histidine Residues within the T4 Endonuclease V Gene: Role in Enzyme-Nontarget DNA Binding. Biochemistry 30:8052-8059, 1991.

Chenevert, J., L. Naumovski, R. Schultz, E. Friedberg. Partial Complementation of the UV Sensitivity of *E. coli* and Yeast Excision Repair Recombinants by the cloned denV gene of Bacteriophage T4. Molecular and General Genetics 203: 163-171, 1986.

Dodson, M. and R. Lloyd. Structure-Function Studies of the T4 endonuclease V Repair Enzyme. Mutation Research 218:49-65, 1989.

Doi, T., A. Recktenwald, Y. Karaki, M. Kikuchi, K. Morikawa, M. Ikehara, T. Inaoka, N. Hori, E. Ohtsuka. Role of the Basic Arluino Acid Cluster and Glu-23 in Pyrimidine Dimer Glycosylase Activity of T4 Endonuclease V. Proceedings of the National Academy of Sciences USA 89:9420-9424, 1992.

Green, A., J. deRiel and E. Henderson. Structure/Function analysis of the Ala$^{116}$ →Lys$^{21}$ of Endonuclease V by Random Targeted Mutagenesis. Nucleic Acids Research 21:727-732, 1993.

Gustafsson, Claes. Protein Expression Using Synthetic Genes. Genetic Engineering News, 25:32, 2005.

Hesterberg, L. K., M. B. Seefeldt, J. F. Carpenter, T. W. Randolph. High-Hydrostatic Pressure Refolding of Proteins. Genetic Engineering News, 25:46-47, 2005.

Hori, N., T. Doi, Y. Karaki, M. Kikuchi, M. Ikehara, E. Ohtsuka. Participation of Glutamic Acid 23 of T4 Endonuclease V in the β-elimination reaction of an abasic site in a synthetic duplex DNA. Nucleic Acids Research 20:4761-4764, 1992.

Inaoka, T., M. Ishida, E. Ohtsuka. Affinity of Single-or Double-stranded Oligodeoxyribonucleotides Containing a Thymine Photodimer for T4 Endonuclease V. The Journal of Biological Chemistry 264:2609-2614, 1989.

Ishida, M., Y. Kanamori, N. Hori, T. Inaoka and E. Ohtsuka. In Vitro and In Vivo Activities of T4 Endonuclease V Recombinants Altered in the C-Terminal Aromatic Region. Biochemistry 29:3817-3821, 1990.

Lapointe, G., T. Mori, D. Evans. Tobacco Plants Expressing T4 Endonuclease V Show Enhanced Sensitivity to Ultraviolet Light and DNA Alkylating Agents. Mutatin Research. 351:19-31, 1996.

Liebig, H-D. and W. Rüiger. Bacteriophage T4 Early Promoter Regions; Consensus Sequences of Promoters and Ribosome-binding Sites. Journal of Molecular Biology, 208:517-536, 1989.

Liszewski, K. Emerging Protein-Expression Technologies. Genetic Engineering News, Volume 23, Number 18, Oct. 15, 2003, page 34.

Lloyd, R. and P. Hanawalt. Expression of the denV Gene of Bacteriophage T4 clond in *Escherichia coli*. Proceedings of the National Academy of Sciences, USA 78:2796-2800, 1981.

Nickolof, J. A. and M. F. Hoekstra, eds. *DNA Damage and Repair*, Volumes I and II Humana Press, Totowa N.J., 1998.

Radany, E., L. Naumovski, J. Love, K. Gutekunst, D. Hall, E. Friedberg. Physical Mapping and Complete Nucleotide Sequence of the denV Gene of Bacteriophage T4. Journal of Virology, 52:846-856, 1984.

Recinos, A., M. Augustine, K. Higgins, R. Lloyd. Expression of the Bacteriophage T4 denV Structural Gene in *Escherichia coli*. Journal of Bacteriology 168:1014-1018, 1986.

Ronen, A. and B. W. Glickman. Human DNA Repair Genes. Environmental and Molecular Mutagenesis 37:241-283, 2001.

Sambrook, J., E. F. Fritsch, T. Maniatis. *Molecular Cloning: A Laboratory Manual* volumes I-III. Cold Spring Harbor Laboratory Press, Cold Spring Harbor, N.Y. 1989.

Sancar, A., L. A. Lindsey-Boltz, K. Unsal-Kacmaz and S. Linn. Molecular Mechanisms of Mammalian DNA Repair and the DNA Damage Checkpoints. Annual Review of Biochemistry. 73:39-85, 2004.

Scopes, R. K. *Protein Purification: Principles and Practices* 3$^{rd}$ edition. Springer-Verlag, N.Y., 1994.

St. John, R. J., J. F. Carpenter, T. W. Randolph. High Pressue Fosters Protein Refolding from Aggregates at High Concentrations. Proc. Natl. Acad. Sci., USA 96:13029-13033, 1999.

Valerie, K., E. Henderson, J. deRiel. Identification, Physical Map Location and Sequence of the denV Gene from Bacteriophage T4. Nucleic Acids Research, 12:8085-8096, 1984.

Valerie, K., J. Stevens, M. Lynch, E. Henderson, J.K. de Riel. Nucleotide sequence and analysis of the 58.3 to 65.5-kb early region of bacteriophage T4. Nucleic Acids Research, 14:8637-8654, 1986a.

Valerie, K., G. Fronko, E. Henderson, J. deRiel. Expression of the denV Gene of Coliphage T4 in UV-Sensitive rad Recombinants of *Saccharomyces cerevisiae*. Molecular and Cellular Biology, 6:3559-3562, 1986b.

Waterman, M. *Introduction to Computational Biology*. CRC Press, Boca Raton Fla. 1995.

Yarosh, D., Boumakis, S., Brown, A., Canning, M., Galvin, J., Both, D., Kraus, E., O'Connor, A., Brown, D. Measurement of UVB-induced DNA damage and its consequences in models of immunosuppression. Methods 28:55-62, 2002.

Yarosh, D., A. O'Connor, L. Alas, C. Potten, P. Wolf. Photoprotection by Topical DNA Repair Enzymes: Molecular Correlates of Clinical Studies. Photochem. Photobiol. 69:136-140, 1999.

PATENT REFERENCES

U.S. Pat. No. 5,308,762. T4 Endonuclease V DNA Repair Enzyme Having Specific Activity at Low Salt Concentrations. 1994.
U.S. Pat. No. 5,077,211. Purification and Administration of DNA Repair Enzymes. 1991 (U.S. Pat. No. '211 patent)
U.S. Pat. No. 5,296,231. Purification and Administration of DNA Repair Enzymes. 1994. (U.S. Pat. No. '231 patent)
U.S. Pat. No. 5,302,389. Methods and Compositions for Treating UV Induced Immuno-suppression. 1994. (U.S. Pat. No. '389 patent)

TABLE 1

Prior Art Rules for Preferred Codon Usage.

| Amino Acid | Abbreviation | Preferred Codon |
|---|---|---|
| Alanine | Ala | GCG |
| Arginine | Arg | CGT |
| Asparagine | Asn | AAC |
| Asparatic Acid | Asp | GAT |
| Cysteine | Cys | TGC |
| Glutamic Acid | Gln | CAG |
| Glutamine | Glu | GAA |
| Glycine | Gly | GGC |
| Histidine | His | CAT |
| Isoleucine | Ile | ATT |
| Leucine | Leu | CTG |
| Lysine | Lys | AAA |
| Methionine | Met | ATG |
| Phenylalanine | Phe | TTT |
| Proline | Pro | CCG |
| Serine | Ser | AGC |
| Threonine | Thr | ACC |
| Tryptophan | Trp | TGG |
| Tyrosine | Tyr | TAT |
| Valine | Val | GTG |

TABLE 2

Present Invention Rules for Preferred Codon Usage.

| Amino Acid | Abbreviation | Preferred Codon |
|---|---|---|
| Group A | | |
| Tyrosine | Tyr | TAC |
| Glycine | Gly | GGT |
| Valine | Val | GTT |
| Serine | Ser | TCT |
| Alanine | Ala | GCT or GCA |
| Group B | | |
| Isoleucine | Ile | ATC |
| Phenylalanine | Phe | TTC |
| Aspartic Acid | Asp | GAG |
| Histidine | His | CAC |

TABLE 3

Amino acid homologies in the T4 endonuclease V subfamily of CPD glycosylases

| AA number | amino acid | Function if known* |
|---|---|---|
| 3 | Arginine | substrate binding |
| 12 | Leucine | |
| 17 | Leucine | |
| 22 | Arginine | substrate binding |
| 23 | Glutamic acid | catalysis |
| 81 | Arginine | |
| 82 | Glycine | |
| 106 | Proline | substrate binding |

*The functional significances of the particular amino acids are described in Atkins Latham and Lloyd, 1994, and Augustine et al., 1991.

TABLE 4

Amino Acid Homologies between Amino Acids 115 and 123 in the Two Subfamilies of CPD Glycosylases

| AA Number | T4 endonuclease V Subfamily Family Amino Acid | *Micrococcus luteus* Subfamily Amino Acid |
|---|---|---|
| 115 | Glutamine or Arginine | |
| 116 | Alanine or Lysine | Lysine |
| 117 | Arginine | {gap} |
| 118 | Isoleucine or Leucine | Leucine |
| 119 | Alanine, Aspartic Acid, Lysine or Leucine | Alanine or Serine |
| 120 | Alanine or Glutamic Acid | Valine, Threonine or Serine |
| 121 | Lysine or Arginine | Arginine |
| 122 | | Serine |
| 123 | | Proline |

TABLE 5

Amino Acid Codon Usage among CPD Glycosylases

CPD Glycosylases from These Organisms and their Related Strains

| Amino Acid | Codon | Phage T4 | Phage RB69 | Chlorella Virus | Bordetella | Prochlorococcus | Haemophilus | Brucella | Pasteurella | Micrococcus | Nitrosomonas | Azoarcus |
|---|---|---|---|---|---|---|---|---|---|---|---|---|
| Group A | | | | | | | | | | | | |
| Tyrosine | TAC | 29% | 0% | 43% | 60% | 33% | 75% | 20% | 25% | 0% | 0% | 50% |
| Glycine | GGT | 86% | 0% | 75% | 0% | 0% | 60% | 17% | 60% | 18% | 14% | 0% |
| Valine | GTT | 71% | 100% | 67% | 14% | 0% | 25% | 25% | 0% | 0% | 38% | 25% |

TABLE 5-continued

Amino Acid Codon Usage among CPD Glycosylases

CPD Glycosylases from These Organisms and their Related Strains

| Amino Acid | Codon | Phage T4 | Phage RB69 | *Chlorella* Virus | *Bordetella* | *Prochlorococcus* | *Haemophilus* | *Brucella* | *Pasteurella* | *Micrococcus* | *Nitrosomonas* | *Azoarcus* |
|---|---|---|---|---|---|---|---|---|---|---|---|---|
| Serine | TCT | 40% | 100% | 0% | 0% | 33% | 0% | 0% | 0% | 0% | 0% | 9% |
| Alanine | GCT or GCA | 85% | 100% | 89% | 5% | 80% | 83% | 35% | 50% | 0% | 54% | 55% |
| | | | | | | Group B | | | | | | |
| Isoleucine | ATC | 31% | 0% | 8% | 33% | 29% | 40% | 60% | 33% | 100% | 67% | 100% |
| Phenylalanine | TTC | 38% | 0% | 33% | 67% | 71% | 25% | 75% | 29% | 100% | 80% | 67% |
| Aspartic Acid | GAC | 13% | 0% | 44% | 67% | 40% | 0% | 100% | 71% | 100% | 0% | 43% |
| Histidine | CAC | 25% | 0% | 0% | 75% | 33% | 50% | 100% | 20% | 100% | 54% | 57% |

TABLE 6

Effect of Most Preferred Embodiments of the Present Invention on Codon Usage in the denV gene

| Amino Acid | Codon | Native denV gene | Recombinant denV gene |
|---|---|---|---|
| Group A | | | |
| Tyrosine | TAC | 29% | 100% |
| Glycine | GGT | 86% | 100% |
| Valine | GTT | 71% | 86% |
| Serine | TCT | 40% | 100% |
| Alanine | GCT or GCA | 85% | 92% |
| Group B | | | |
| Isoleucine | ATC | 31% | 100% |
| Phenylalanine | TTC | 38% | 100% |
| Aspartic acid | GAC | 13% | 88% |
| Histidine | CAC | 25% | 100% |

TABLE 7

Comparison of Sonication to Stream Mixing

| | Sonication | Stream Mixing | Stream Mixing/ Sonication |
|---|---|---|---|
| Total Protein (mg/ml) | 6.9 | 17.5 | 250% |
| T4 endonuclease V (mg/ml) | 1.1 | 7.8 | 710% |
| Purity | 20.4% | 44.3% | 220% |
| Unit Activity (U/ml × 10$^6$) | 2,320 | 11,700 | 500% |
| Specific Activity (U/ug × 10$^3$) | 336 | 667 | 200% |

TABLE 8

Comparison of native and recombinant gene expression for yield and purity.

| | Protein Yield | T4 endonuclease V | Purity: Percent of total protein |
|---|---|---|---|
| Lysate | | | |
| Native | 412,000 mg | 3,710 mg | 0.9% |
| Recombinant | 659,000 mg | 237,000 mg | 36.0% |
| Clarification | | | |
| Native | 53,900 mg | 3,080 mg | 5.7% |
| Recombinant | 90,800 mg | 50,900 mg | 56.0% |
| Gel Filtration | | | |
| Native | 2,170 mg | 213 mg | 9.8% |
| Recombinant | 8,520 mg | 8,180 mg | 96.0% |
| Affinity Chromatography | | | |
| Native | 237 mg | 179 mg | 76.0% |
| Recombinant | 4,030 mg | 3,990 mg | 99.0% |

TABLE 9

Formulation for Delivery of Liposomes Containing One or More CPD Glycosylases, e.g., T4 Endonuclease V, to Skin

| Step | Percent | Ingredient |
|---|---|---|
| 1 | 79.5 | Deionized water |
| 1 | 0.90 | CARBOPOL 981 NF |
| 2 | 9.66 | 10-fold concentrate Phosphate Buffer Saline |
| 2 | 1.00 | Phenoxyethanol |
| 3 | 0.60 | Triethanolamine |
| 4 | 5.00 | CARBOWAX PEG-400 |
| 5 | 3.34 | Liposomes containing T4 endonuclease V protein, 34 micrograms protein per ml, 3 trillion liposomes per ml |
| 6 | qs | Triethanolamine |

Procedure:

1. In kettle, combine Step 1 ingredients and heat to 60° C. Mix with propeller at medium to high speed.
2. Add Step 2 ingredients to batch and mix until dispersed.
3. Add Step 3 ingredient to batch and continue mixing until solution is clear and uniform. Hold temperature at 60° C.
4. Add Step 4 ingredient to batch, mix until clear and uniform. Cool batch to 20° C.
5. Add Step 5 ingredient to batch, mix gently at slow speed until uniform.
6. Adjust pH to 7.6–7.8 if necessary using Step 6 ingredient.

What is claimed is:

1. An isolated, synthetic, and/or recombinant polynucleotide comprising:
   (a) a nucleotide sequence encoding a native amino acid sequence of a cyclobutane pyrimidine dimer (CPD) glycosylase protein from an organism selected from the group consisting of Bacteriophage T4, Bacteriophage RB69, *Paramecium bursaria Chlorella* virus I, *Prochlorus marinus*, *Bordetella parapertussis*, *Haemophilus ducreyi*, *Brucella melitensis*, *Pasteurella multocida*, *Micrococcus luteus*, *Nitrosomonas europeaea* and *Azoarcus* sp. EbN1; or
   (b) a complement of said nucleotide sequence, wherein the complement and the nucleotide sequence consist of the same number of nucleotides and are 100% complementary;
   wherein:
   (I) Groups A and B represent the following codons for the following amino acids:

| Amino Acid | Codon |
|---|---|
| Group A | |
| Tyrosine | TAC |
| Glycine | GGT |
| Valine | GTT |
| Serine | TCT |
| Alanine | GCT or GCA |
| Group B | |
| Isoleucine | ATC |
| Phenylalanine | TTC |
| Aspartic Acid | GAC |
| Histidine | CAC | and
   (II) the nucleotide sequence comprises:
   (a) at least two codons from Group A for more than 45% of the occurrences of the amino acid coded by the codon in the CPD glycosylase protein and at least two codons from Group B for more than 45% of the occurrences of the amino acid coded by the codon in the CPD glycosylase protein; or
   (b) at least three codons from Group A for more than 35% of the occurrences of the amino acid coded by the codon in the CPD glycosylase protein and at least three codons from Group B for more than 35% of the occurrences of the amino acid coded by the codon in the CPD glycosylase protein.

2. The polynucleotide of claim 1 wherein in accordance with subparagraph (II)(a), the nucleotide sequence comprises at least two codons from Group A for more than 75% of the occurrences of the amino acid coded by the codon in the CPD glycosylase protein and at least two codons from Group B for more than 75% of the occurrences of the amino acid coded by the codon in the CPD glycosylase protein.

3. The polynucleotide of claim 1 wherein in accordance with subparagraph (II)(b), the nucleotide sequence comprises at least three codons from Group A for more than 45% of the occurrences of the amino acid coded by the codon in the CPD glycosylase protein and at least three codons from Group B for more than 45% of the occurrences of the amino acid coded by the codon in the CPD glycosylase protein.

4. The polynucleotide of claim 1 wherein in accordance with subparagraph (II)(b), the nucleotide sequence comprises at least three codons from Group A for more than 75% of the occurrences of the amino acid coded by the codon in the CPD glycosylase protein and at least three codons from Group B for more than 75% of the occurrences of the amino acid coded by the codon in the CPD glycosylase protein.

5. An isolated, synthetic, or recombinant polynucleotide comprising:
(a) a nucleotide sequence encoding a native amino acid sequence of a cyclobutane pyrimidine dimer (CPD) glycosylase protein from an organism selected from the group consisting of Bacteriophage T4, Bacteriophage RB69, *Paramecium bursaria Chlorella* virus I, *Prochlorus marinus*, *Bordetella parapertussis*, *Haemophilus ducrevi*, *Brucella melitensis*, *Pasteurella multocida*, *Micrococcus luteus*, *Nitrosomonas europeaea* and *Azoarcus* sp. EbN1; or
(b) a complement of said nucleotide sequence, wherein the complement and the nucleotide sequence consist of the same number of nucleotides and are 100% complementary;
wherein the nucleotide sequence comprises the following codons for more than 75% of the occurrences of the amino acid coded by the codon in the CPD glycosylase protein:

| Amino Acid | Codon |
| --- | --- |
| Tyrosine | TAC |
| Glycine | GGT |
| Valine | GTT |
| Serine | TCT |
| Alanine | GCT or GCA |
| Isoleucine | ATC |
| Phenylalanine | TTC |
| Aspartic Acid | GAC |
| Histidine | CAC. |

6. The polynucleotide of claim 1 or 5 wherein Group C represents the following codons for the following amino acids:

| Amino Acid | Codon |
| --- | --- |
| Arginine | CGT |
| Asparagine | AAC |
| Cysteine | TGC |
| Glutamic Acid | CAG |
| Glutamine | GAA |
| Leucine | CTG |
| Lysine | AAA |
| Methionine | ATG |
| Proline | CCG |
| Threonine | ACC |
| Tryptophan | TGG | and the nucleotide sequence comprises at least one codon from Group C for more than 75% of the occurrences of the amino acid coded by the codon in the CPD glycosylase protein.

7. The polynucleotide of claim 1 or 5 wherein the CPD glycosylase protein is T4 endonuclease V or *Micrococcus luteus* UV endonuclease.

8. An isolated, synthetic, or recombinant polynucleotide comprising the nucleotide sequence of SEQ ID NO: 1 or a complement of the nucleotide sequence, wherein the complement and the nucleotide sequence consist of the same number of nucleotides and are 100% complementary.

9. A method for transforming an isolated cell comprising transforming the cell with the polynucleotide of claim 1 or 5.

10. A vector comprising the polynucleotide of claim 1 or 5.

11. An isolated host cell comprising the vector of claim 10.

12. A method of producing a CPD glycosylase protein comprising culturing cells according to claim 11 under conditions where the cells produce the CPD glycosylase protein and collecting the protein so produced.

13. A DNA construct comprising the polynucleotide of claim 1 or 5 operably linked to at least one regulatory sequence.

14. An isolated host cell comprising the DNA construct of claim 13.

15. A method of producing a CPD glycosylase protein comprising culturing cells according to claim 14 under conditions where the cells produce the CPD glycosylase protein and collecting the protein so produced.

16. An isolated, synthetic, or recombinant polynucleotide comprising:
(a) a nucleotide sequence encoding a T4 endonuclease V protein having the amino acid sequence of SEQ ID NO: 2; or
(b) a complement of the nucleolide sequence, wherein the complement and the nucleotide sequence consist of the same number of nucleotides and are 100% complementary;
wherein:
(I) Groups A and B represent the following codons for the following amino acids:

| Amino Acid | Codon |
| --- | --- |
| Group A | |
| Tyrosine | TAC |
| Glycine | GGT |
| Valine | GTT |
| Serine | TCT |
| Alanine | GCT or GCA |
| Group B | |
| Isoleucine | ATC |
| Phenylalanine | TTC |
| Aspartic Acid | GAC |
| Histidine | CAC | and
(II) the nucleotide sequence comprises:
(a) at least two codons from Group A for more than 45% of the occurrences of the amino acid coded by the codon in the T4 endonuclease V protein and at least two codons from Group B for more than 45% of the occurrences of the amino acid coded by the codon in the T4 endonuclease V protein; or
(b) at least three codons from Group A for more than 35% of the occurrences of the amino acid coded by the codon in the T4 endonuclease V protein and at least three codons from Group B for more than 35% of the occurrences of the amino acid coded by the codon in the T4 endonuclease V protein.

* * * * *

SEQUENCE LISTING

<160> NUMBER OF SEQ ID NOS: 4

<210> SEQ ID NO 1
<211> LENGTH: 417
<212> TYPE: DNA
<213> ORGANISM: Artificial Sequence
<220> FEATURE:
<223> OTHER INFORMATION: Recombinant DNA sequence for CPD glycosylase of
      the bacteriophage T4 denV gene as modified by AGI

<400> SEQUENCE: 1

```
atgacccgta tcaacctgac cctggtttct gaactggctg accagcacct gatggctgaa      60
taccgtgaac tgccgcgtgt tttcggtgct gtacgtaaac acgttgctaa cggtaaacgt     120
gttcgtgact tcaaaatctc tccgaccttc atcctgggtg ctggtcacgt taccttcttt     180
tacgacaaac tggaattcct gcgtaaacgt cagatcgaac tgatcgctga atgcctgaaa     240
cgtggtttca acatcaaaga caccactgtt caggatatct ctgacatccc gcaggaattc     300
cgtggtgact acatcccgca cgaagcttct atcgcaatct ctcaggctcg tctggacgaa     360
aaaatcgctc agcgtccgac ctggtacaaa tattacggta agcaatcta cgcttaa        417
```

<210> SEQ ID NO 2
<211> LENGTH: 138
<212> TYPE: PRT
<213> ORGANISM: Bacteriophage T4

<400> SEQUENCE: 2

```
Met Thr Arg Ile Asn Leu Thr Leu Val Ser Glu Leu Ala Asp Gln His
1               5                   10                  15

Leu Met Ala Glu Tyr Arg Glu Leu Pro Arg Val Phe Gly Ala Val Arg
            20                  25                  30

Lys His Val Ala Asn Gly Lys Arg Val Arg Asp Phe Lys Ile Ser Pro
        35                  40                  45

Thr Phe Ile Leu Gly Ala Gly His Val Thr Phe Phe Tyr Asp Lys Leu
    50                  55                  60

Glu Phe Leu Arg Lys Arg Gln Ile Glu Leu Ile Ala Glu Cys Leu Lys
65                  70                  75                  80

Arg Gly Phe Asn Ile Lys Asp Thr Thr Val Gln Asp Ile Ser Asp Ile
                85                  90                  95

Pro Gln Glu Phe Arg Gly Asp Tyr Ile Pro His Glu Ala Ser Ile Ala
            100                 105                 110

Ile Ser Gln Ala Arg Leu Asp Glu Lys Ile Ala Gln Arg Pro Thr Trp
        115                 120                 125

Tyr Lys Tyr Tyr Gly Lys Ala Ile Tyr Ala
    130                 135
```

<210> SEQ ID NO 3
<211> LENGTH: 417
<212> TYPE: DNA
<213> ORGANISM: Bacteriophage T4

<400> SEQUENCE: 3

```
atgactcgta tcaaccttac tttagtatct gaattggctg accaacactt aatggctgaa      60
tatcgtgaat tgccgcgtgt ttttggtgca gttcgtaagc atgttgctaa cggtaaacgt     120
gttcgtgatt tcaaaatcag tcctactttt atccttggcg caggtcatgt tacattcttt     180
tacgataagc tcgagttctt acgtaaacgt caaatcgagc ttatagctga atgtttaaaa     240
```

```
cgtggttta   atatcaagga  tactacagtc  caggatatta  gtgatattcc  tcaggaattc    300
cgtggtgatt  atattcccca  tgaagcttct  attgctatat  cacaagctcg  tttagatgaa    360
aaaattgcac  aacgtcctac  ttggtacaaa  tactacggta  aggcgattta  tgcataa       417

<210> SEQ ID NO 4
<211> LENGTH: 417
<212> TYPE: DNA
<213> ORGANISM: Artificial Sequence
<220> FEATURE:
<223> OTHER INFORMATION: Recombinant DNA sequence for CPD glycosylase of
      the bacteriophage T4 denV gene as modified by Inaoka

<400> SEQUENCE: 4
atgacgcgta  tcaaccttac  tttagtatcc  gagttagctg  accaacactt  aatggctgaa    60
taccgtgaat  tgccgcgtgt  ttttggtgca  gttcgtaagc  acgtagcaaa  cggtaaacgt    120
gttcgtgatt  tcaaaatcag  tcctactttt  atccttggcg  caggtcatgt  tacattcttc    180
tacgataagc  tcgagttctt  acgcaagcgt  caaattgagc  ttatagctga  atgtttgaaa    240
cgtggtttca  atatcaagga  tactacagtc  caggacatca  gtgacattcc  tcaagaattc    300
cgtggtgatt  atattcccca  tgaagcttct  attgctatat  cacaagctcg  tttagatgaa    360
aaaattgcac  aacgtcctac  ttggtacaaa  tactacggta  aggcgattta  tgcagaa       417
```